(12) United States Patent
Yan et al.

(10) Patent No.: US 12,394,057 B2
(45) Date of Patent: Aug. 19, 2025

(54) METHOD, DEVICE, AND SYSTEM FOR PROCESSING MEDICAL IMAGE

(71) Applicant: OUR UNITED CORPORATION, Xi'an (CN)

(72) Inventors: Hao Yan, Xi'an (CN); Wen Wang, Xi'an (CN); Weiqun Yang, Xi'an (CN); Ningwei He, Xi'an (CN); Gaowa Siqin, Xi'an (CN); Jinsheng Li, Xi'an (CN)

(73) Assignee: OUR UNITED CORPORATION, Xi'an (CN)

( * ) Notice: Subject to any disclaimer, the term of this patent is extended or adjusted under 35 U.S.C. 154(b) by 406 days.

(21) Appl. No.: 17/822,259

(22) Filed: Aug. 25, 2022

(65) Prior Publication Data
US 2023/0064516 A1 Mar. 2, 2023

(30) Foreign Application Priority Data

Aug. 25, 2021 (CN) .......................... 202110984265.X

(51) Int. Cl.
| | |
|---|---|
| *A61B 17/00* | (2006.01) |
| *A61N 5/10* | (2006.01) |
| *G06T 7/00* | (2017.01) |
| *G06T 7/12* | (2017.01) |
| *G06T 7/13* | (2017.01) |
| *G06T 7/33* | (2017.01) |
| *G16H 20/40* | (2018.01) |

(Continued)

(52) U.S. Cl.
CPC .............. *G06T 7/0016* (2013.01); *G06T 7/13* (2017.01); *G06T 7/337* (2017.01); *G16H 30/40* (2018.01); *G06T 2207/30004* (2013.01)

(58) Field of Classification Search
None
See application file for complete search history.

(56) References Cited

U.S. PATENT DOCUMENTS

| | | | |
|---|---|---|---|
| 6,600,810 B1 | 7/2003 | Hughes | |
| 2007/0014452 A1* | 1/2007 | Suresh | .................. G06T 7/0012 382/128 |

(Continued)

FOREIGN PATENT DOCUMENTS

| | | |
|---|---|---|
| CN | 103007440 A | 4/2013 |
| CN | 103079643 A | 5/2013 |

(Continued)

OTHER PUBLICATIONS

China National Intellectual Property Administration, Notification to grant patent right for invention of Chinese application No. 202110984264.5 issued on Apr. 24, 2024, which is foreign counterpart application of this US application.

(Continued)

*Primary Examiner* — Mohammed Rachedine
(74) *Attorney, Agent, or Firm* — Kolitch Romano Dascenzo Gates LLC

(57) ABSTRACT

Provided is a method for processing a medical image. In the method, a processing result is acquired by processing, without acquiring a user operation, an acquired medical image of a target object, and subsequently, the processing result is output in response to acquiring a user operation triggered by a user for viewing a processed medical image.

18 Claims, 10 Drawing Sheets

(51) Int. Cl.
    *G16H 30/40* (2018.01)
    *G16H 40/63* (2018.01)
    *G16H 50/50* (2018.01)

(56) References Cited

U.S. PATENT DOCUMENTS

| | | | |
|---|---|---|---|
| 2012/0043482 | A1 | 2/2012 | Prince et al. |
| 2015/0238158 | A1* | 8/2015 | Zhou .................... G06T 7/73 382/131 |
| 2017/0340902 | A1 | 11/2017 | Vilsmeier et al. |
| 2019/0175944 | A1 | 6/2019 | Towe et al. |
| 2021/0016110 | A1 | 1/2021 | Gou et al. |
| 2021/0202092 | A1* | 7/2021 | Wallack .................. G16H 30/20 |
| 2022/0092745 | A1* | 3/2022 | Tanaka .................. G06T 7/0016 |
| 2022/0143426 | A1 | 5/2022 | Liu et al. |

FOREIGN PATENT DOCUMENTS

| | | | | |
|---|---|---|---|---|
| CN | 105931237 | A | | 9/2016 |
| CN | 108635681 | A | | 10/2018 |
| CN | 109727277 | A | | 5/2019 |
| CN | 109908497 | A | | 6/2019 |
| CN | 110146869 | A | | 8/2019 |
| CN | 110559077 | A | | 12/2019 |
| CN | 111240370 | A | | 6/2020 |
| CN | 111408065 | A | | 7/2020 |
| CN | 112089991 | A | | 12/2020 |
| CN | 112180362 | A | | 1/2021 |
| CN | 110215621 | B | * | 5/2021 .............. A61B 6/032 |
| CN | 112837391 | A | | 5/2021 |
| CN | 112867537 | A | | 5/2021 |
| CN | 112971982 | A | | 6/2021 |
| CN | 215117588 | U | | 12/2021 |
| CN | 114173868 | A | | 3/2022 |
| CN | 114255172 | A | * | 3/2022 |
| WO | WO-2022082533 | A1 | * | 4/2022 |
| WO | WO-2022141373 | A1 | * | 7/2022 .............. G06T 11/008 |

OTHER PUBLICATIONS

China National Intellectual Property Administration, First office action of Chinese application No. 202110687672.4 issued on May 23, 2024, which is foreign counterpart application of this US application.

China National Intellectual Property Administration, First office action of Chinese application No. 202210283789.0 issued on Jul. 3, 2024, which is foreign counterpart application of this US application.

Cui, Wei-jie et al., "The configuration designs for multileaf collimators", Medical Equipment vol. 22, No. 2, Feb. 15, 2009.

Gu, Guo-hua et al., "Camera parameter calibration based on two-dimensional rotating platform", Optics and Precision , Engineering, vol. 25, No. 7, Jul. 15, 2017.

Tao, Shengxiang et al., "Position-validating method in radiotherapy based on binocular vision photogrammetry", Nuclear Techniques, vol. 30, No. 3, Mar. 10, 2007, Entire document.

\* cited by examiner

METHOD, DEVICE, AND SYSTEM FOR PROCESSING MEDICAL IMAGE

CROSS-REFERENCE TO RELATED APPLICATION

The present disclosure is based on and claims priority to Chinese Patent Application No. 202110984265.X, filed on Aug. 25, 2021 and entitled "METHOD, DEVICE, AND SYSTEM FOR PROCESSING MEDICAL IMAGE", the disclosure of which is incorporated herein by reference in its entirety.

TECHNICAL FIELD

The present disclosure relates to a method, device, and system for processing a medical image.

BACKGROUND

Prior to performing radiation treatment on an affected part of a patient, a radiation treatment plan needs to be developed, and an accuracy of the radiation treatment plan may directly affect the effect of radiation treatment.

SUMMARY

Embodiments of the present disclosure provide a method, device, and system for processing a medical image. The technical solutions are described as follows.

According to some embodiments of the present disclosure, a method for processing a medical image is provided. The method includes: acquiring a medical image of a target object; acquiring a processing result by processing, without acquiring a user operation, the medical image using an image processing mode corresponding to the medical image of the target object; and outputting the processing result in response to acquiring a user operation triggered by a use for viewing a processed medical image.

According to some embodiments of the present disclosure, a method for processing a medical image is provided. The method includes: acquiring a medical image of a target object; acquiring a processing result by processing, without acquiring a user operation, the medical image using an image processing mode corresponding to the medical image of the target object, wherein the image processing mode includes automatic registration and/or automatic contouring; and saving the processing result.

According to some embodiments of the present disclosure, a system for processing a medical image is provided. The system includes a server end and a user end, wherein the server end is configured to acquire a medical image of a target object, and acquire a processing result by processing, without acquiring a user operation, the medical image using an image processing mode corresponding to the medical image of the target object; the user end is configured to acquire a user operation triggered by a user for viewing a processed medical image, and send the user operation to the server end; the server end is further configured to output the processing result in response to acquiring the user operation; and the user end is further configured to acquire the processing result and display a medical image corresponding to the processing result.

According to some embodiments of the present disclosure, a device for processing a medical image is provided. The device includes: a processor and a memory configured to store an instruction executed by the processor, wherein the processor, when executing the instruction stored in the memory, is caused to perform the method for processing the medical image according to above embodiments.

According to some embodiments of the present disclosure, a non-volatile computer-readable storage medium storing an instruction therein is provided, and the instruction, when executed on a computer, causes the computer to perform the method for processing the medical image according to above embodiments.

According to some embodiments of the present disclosure, a computer program product is provided. The computer program product includes an instruction, wherein the computer program product, when run on a computer, causes the computer to execute the method for processing the medical image according to above embodiments.

DETAILED DESCRIPTION

For clearer descriptions of the objectives, technical solutions, and advantages in the present disclosure, the embodiments of the present disclosure are described in detail hereinafter in combination with the accompanying drawings.

In the related art, a physician triggers a processing operation prior to developing a radiation treatment plan, and a system for processing a medical image acquires a processing result of an image by processing the acquired image of the affected part based on the acquired processing operation. For example, the processing operation is a registration operation or a contouring operation, and correspondingly, the processing result is a registration result or a contouring result. Finally, the physician develops the radiation treatment plan based on the processing result of the image.

However, the process of image processing performed by the system for processing the medical image needs to be performed based on the physician operation, and thus the efficiency is poor.

Figure 1:
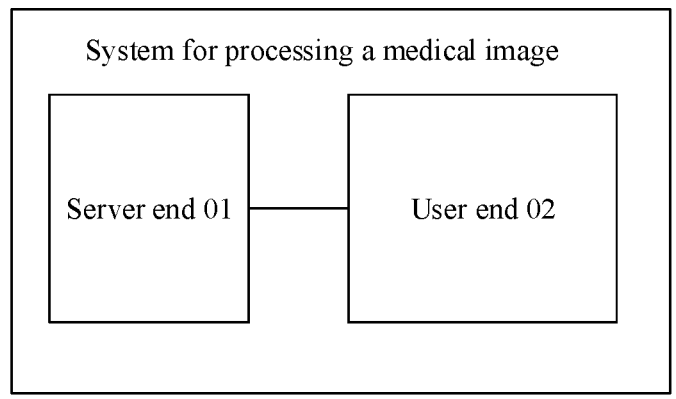
FIG. 1 is a schematic structural diagram of a system for processing a medical image according to some embodiments of the present disclosure.

FIG. 1 is a schematic structural diagram of a system for processing a medical image according to some embodiments of the present disclosure. Referring to FIG. 1, the system for processing the medical image includes: a server end 01 and a user end 02. A communication connection is established between the server end 01 and the user end 02 via a wired or wireless network.

In some embodiments, the user end 02 is a smart phone, a computer, a tablet computer, or the like. The server end 01 is one server, a server cluster of several servers, or a cloud computing service center.

The server end 01 is configured to acquire a medical image of a target object, and acquire a processing result by processing, without acquiring a user operation, the medical image using an image processing mode corresponding to the medical image of the target object.

The user end 02 is configured to acquire the user operation triggered by a user for viewing a processed medical image, and send the user operation to the server end 01.

The server end 01 is further configured to output the processing result in response to acquiring the user operation.

The user end 02 is further configured to acquire the processing result and display a medical image corresponding to the processing result.

In some embodiments, the server end 01 is configured to: acquire a first medical image and a second medical image of the target object, wherein the first medical image and the second medical image are images acquired by imaging the target object using different imaging modes and/or in different time periods, that is, the first medical image and the second medical image are images of different modalities; automatically register the first medical image and the second medical image; and acquire a contour of at least one medical image by automatically contouring at least one of the first medical image and the second medical image. The user end 02 is configured to acquire a first user operation triggered by the user for viewing a contoured image of the target object and send the first user operation to the server end 01. The server end 01 is further configured to output the contoured image of the target. object in response to acquiring the first user operation triggered by the user for viewing the contoured image of the target object. The contoured image of the target object is a superimposed image of an automatically registered first medical image and/or an automatically registered second medical image with the contour of the at least one medical image. The user end 02 is further configured to acquire and display the contoured image of the target object.

It should be noted that the server end 01 may acquire the processing result by processing, without acquiring any user operation, the medical image using an image processing mode corresponding to the medical image of the target object. That is, the system for processing the medical image according to the embodiments of the present disclosure may automatically acquire and process the image without acquiring the user (for example, physician) operation. The system for processing the medical image may acquire the image fully automatically and process the acquired image.

Afterwards, the user who wants to view the processed medical image triggers, via the user end 02, a user operation for viewing the processed medical image. The server end 01 directly outputs the processing result of the medical image to the user end 02 in response to receiving the user operation triggered by the user for viewing the processed medical image. The user end 02 displays, in response to acquiring the processing result front the server 01, the medical image corresponding to the processing result. Thus, the user determines the reliability of image processing based on the medical image corresponding to the processing result displayed by the user end 02.

In the embodiments of the present disclosure, the server end 01 in the system for processing the medical image is a cloud server. That is, the server 01 is disposed on a cloud.

Figure 2:
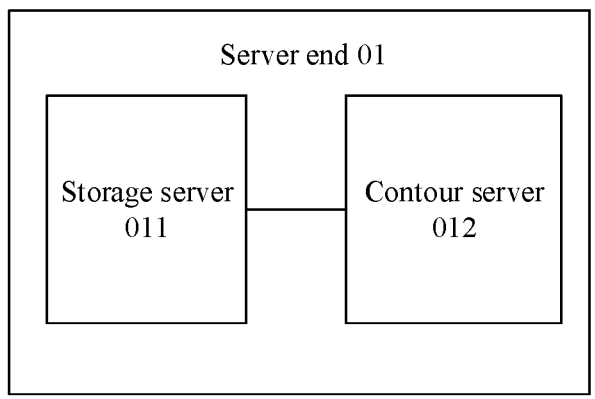
FIG. 2 is a schematic structural diagram of a server end according to some embodiments of the present disclosure.

Referring to FIG. 2, the server end 01 includes a storage server 011 and a contour server 012, and a communication connection is established between the storage server 011 and the contour server 012 via a wired or wireless network.

In some embodiments, the contour server 012 is one server, or a server cluster of several servers. In some embodiments, the contour server 012 is a cloud server. That is, the contour server 012 is disposed on a cloud. In some embodiments, the contour server 012 is a local server. That is, the contour server 012 is disposed on a local end. In some embodiments, the storage server 011 is one server, or a server cluster of several servers. In some embodiments, the storage server 011 is a local server. That is, the storage server 011 may be disposed on a local end.

In some embodiments, the storage server 011 is a digital imaging and communications in medicine (DICOM) server.

In some embodiments, the storage server 011 is configured to store the medical image of the target object. The contour server 012 is configured to acquire the medical image of the target object, and acquire a processing result by processing, without acquiring a user operation, the medical image using an image processing mode corresponding to the medical image of the target object. The storage server 011 is further configured to acquire and store the processing result. The contour server 012 is further configured to acquire the processing result from the storage server 011 and output the processing result to the user end 02 in response to acquiring a user operation triggered by a user for viewing the processed medical image.

Figure 3:
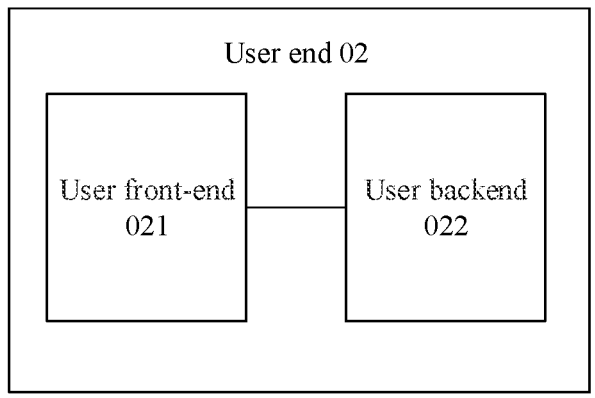
FIG. 3 is a schematic structural diagram of a user end according to some embodiments of the present disclosure.

Referring to FIG. 3, the user end 02 includes a user front-end 021 and a user backend 022. The user front-end 021 is configured to acquire the user operation triggered by the user for viewing the processed medical image and send the user operation to the server end 01 via the user backend 022. The user backend 022 is configured to acquire the processing result from the server end 01 and acquire a medical image corresponding to the processing result by processing the medical image of the target object according to the processing result.

In some embodiments, the user front-end 021 is a stereo display device, and the user backend 022 is a processing device. In some embodiments, the user front-end 021 is an augmented reality (AR) and virtual reality (VR) device to present a stereo display effect.

In the embodiments of the present disclosure, the processing result is an image or a parameter. In the case that the processing result is a parameter (for example, the processing result is an offset and a deformation field that are acquired by image registration), the user backend 022 acquires the medical image corresponding to the processing result by processing the processing result. Thus, the user front-end 021 displays a medical image corresponding to the processing result.

In summary, the embodiments of the present disclosure provide the system for processing the medical image. The system acquires the processing result by processing, without acquiring the user operation, the acquired medical image of the target object, and subsequently, outputs the processing result in response to acquiring the user operation triggered by the user for viewing the processed medical image. That is, in the system for processing the medical image according to the embodiments of the present disclosure, the medical image is automatically processed without acquiring the user operation, and thus a high efficiency of image processing is achieved.

Figure 4:
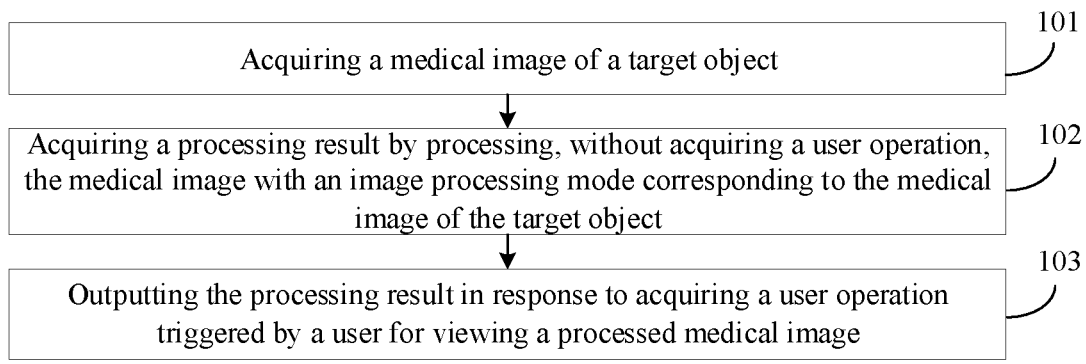
FIG. 4 is a flowchart of a method for processing a medical image according to some embodiments of the present disclosure.

FIG. 4 is a flowchart of a method for processing a medical image according to some embodiments of the present disclosure. The method is applicable to the server end 01 in the system for processing the medical image shown in FIG. 1. That is, the server end 01 may implement the following method for processing the medical image. Referring to FIG. 4, the method includes the following steps.

In S101, a medical image of a target object is acquired.

In the embodiments of the present disclosure, the medical image of the target object is an image acquired by imaging the target object via an imaging apparatus. The server 01 acquires the medical image of the target object from the imaging apparatus.

In some embodiments, the imaging apparatus is a separate apparatus or an imaging apparatus integrated in a radiation treatment device.

In S102, a processing result is acquired by processing, without acquiring a user operation, the medical image using an image processing mode corresponding to the medical image of the target object.

In the embodiments of the present disclosure, the server end 01 acquires the processing result by processing, without acquiring any user operation, the medical image using an image processing mode corresponding to the medical image of the target object.

In some embodiments, the image processing mode includes at least one of image registration, image contouring, and an adjustment of definition and contrast of the image. Correspondingly, the processing result includes a registration result of image registration, a contouring result of image contouring, and an image with adjusted definition and contrast.

In some embodiments, the server end 01 acquires a contouring result of the medical image of the target image by performing, without acquiring the user operation, image contouring (automatic image contouring) on the medical image of the target object.

In S103, the processing result is output in response to acquiring the user operation triggered by the user for viewing the processed medical image.

In the embodiments of the present disclosure, the user who wants to view the processing result triggers, via the user end 02, a user operation for viewing the processed medical image. The server end 01 outputs the processing result in response to acquiring the user operation triggered by the user for viewing the processed medical image. Furthermore, the user end 02 acquires and displays the processing result. Thus, the user develops a radiation treatment plan based on the content displayed by the user end 02.

In some embodiments, the user operation is an operation for opening software in the user end 02 by the user.

In summary, the embodiments of the present disclosure provide the method for processing the medical image. In the method, the processing result is acquired by processing, without acquiring the user operation, the acquired medical image of the target object, and subsequently, the processing result is output in response to acquiring the user operation triggered by the user for viewing the processed medical image. That is, in the method for processing the medical image according to the embodiments of the present disclosure, the medical image is automatically processed without acquiring the user operation, and thus a high efficiency of image processing is achieved.

Figure 5:
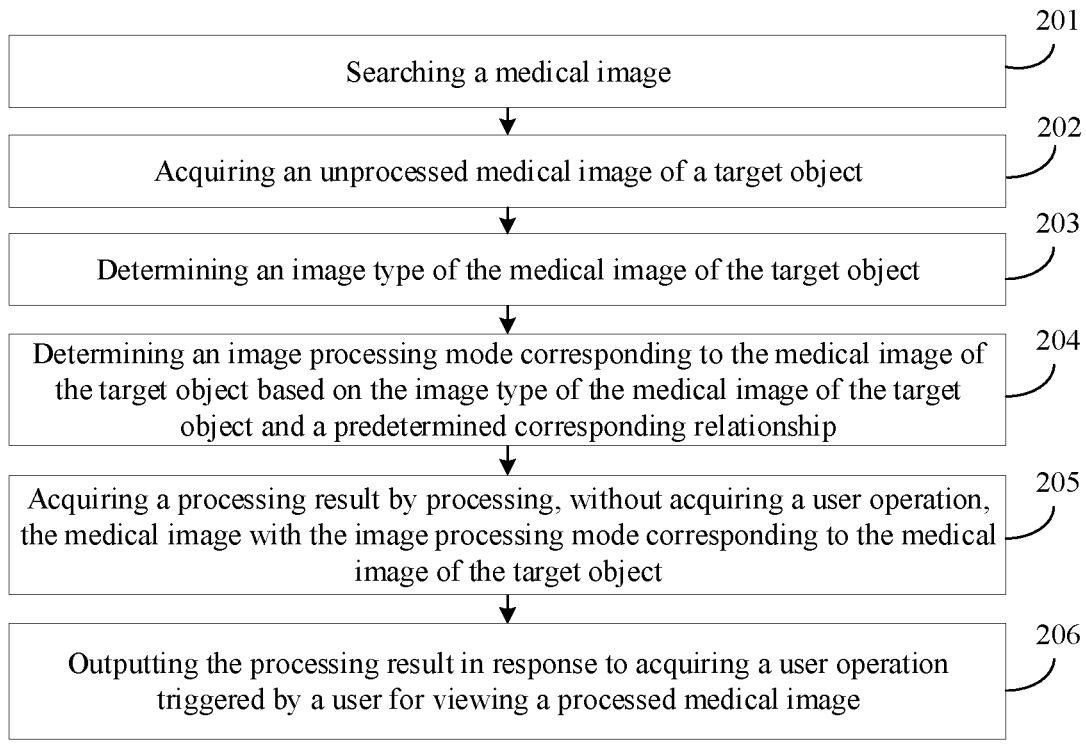
FIG. 5 is a flowchart of another method for processing a medical image according to some embodiments of the present disclosure.

FIG. 5 is a flowchart of another method for processing a medical image according to some embodiments of the present disclosure. The method is applicable to the server end 01 in the system for processing the medical image shown in FIG. 1. That is, the server end 01 may implement the following method for processing the medical image. Referring to FIG. 5, the method includes the following steps.

In S201, a medical image is searched.

In the embodiments of the present disclosure, the storage server 011 of the server end 01 stores an image acquired by imaging via an imaging apparatus. The contour server 012 of the server end 01 searches for the medical image from the storage server 011.

In S202, an unprocessed medical image of a target object is acquired.

In the embodiments of the present disclosure, the storage server 011 of the server end 01 also stores the processing result of the processed medical image of the target object. Thus, the contour server 012 acquires the unprocessed medical image of the target object from the storage server 011. That is, the contour server 012 acquires the medical image of the target object, of which the corresponding processing result is not stored in the storage server 011.

In S203, an image type of the medical image of the target object is determined.

In the embodiments of the present disclosure, the server end 01 determines the image type of the medical image of the target object in response to acquiring the unprocessed medical image of the target object.

The image type of the medical image of the target object may include:

type I: an image acquired by imaging the target object using a same imaging mode in a same time period;

type II: an image acquired by imaging the target object using the same imaging mode in different time periods;

type III: an image acquired by imaging the target object using different imaging modes in the same time period; and type IV: an image acquired by imaging the target object using different imaging modes in different time periods.

It should be noted that, in some embodiments, the same time period represents a shorter time period. For example, the duration of the same time period is one day, e.g., a set of CT images of the target object taken on a day. In some embodiments, the same time period includes different moments in adaptive radiation treatment. A time interval between different time periods may be long. In some embodiments, the time interval is longer than one day, such as, a set of images of the target object taken at different fractions of fractional radiation treatment. The time interval between different time periods is a duration between an end moment of one time period and a start moment of another time period, such as, a duration for treatment of a target spot/target region.

In the case that the image type is type I, the image acquired by imaging is one image. In the case that the image type is type II, type III, or type IV, the image acquired by imaging includes at least two images.

In some embodiments, in the case that the image type is image type II, type III, or type IV, the medical image of the target object includes a first medical image and a second medical image. The first medical image and the second medical image are acquired by imaging, via the imaging apparatuses of the same type, the target object in different time periods. In some embodiments, the first medical image and the second medical image are acquired by imaging, via the imaging apparatuses of different types, the target object in the same time period. In some embodiments, the first medical image and the second medical image are acquired by imaging, via the imaging apparatuses of different types, the target object in different time periods.

It should be noted that the imaging apparatus may be a stand-alone device or an imaging apparatus integrated in a radiation treatment device.

In some embodiments, the imaging apparatus is a computed tomography (CT) device, a magnetic resonance (MR) device, a positron emission tomography-computed tomography (PET-CT) device, and the like. Modes for imaging the image by the devices of different types are different. A CT image is acquired by imaging using a CT device, a MR image is acquired by imaging using a MR device, and a PET-CT image is acquired by imaging using a PET-CT device.

In some embodiments, the first medical image and the second medical image are images acquired by imaging the target object in different time periods. For example, the first medical image and the second medical image are images acquired by imaging the target object before and after treatment respectively, or the first medical image and the second medical image are images acquired by imaging the target object in different time periods in adaptive radiation treatment respectively. Based on the first medical image and the second medical image, it is convenient for the user to determine changes of a lesion of the target object in different time periods. In some embodiments, the first medical image and the second medical image are also images acquired by imaging the target object in the same time period.

In S204, an image processing mode corresponding to the medical image of the target object is determined based on the image type of the medical image of the target object and a predetermined corresponding relationship.

In the embodiments of the present disclosure, the predetermined corresponding relationship is a predefined corresponding relationship between the image type and the image processing mode. The server end 01 determines a target image type of the medical image of the target object based on the image type of the medical image of the target object and the predetermined corresponding relationship, and determines the image processing mode corresponding to the target image type as the image processing mode corresponding to the medical image of the target object.

In some embodiments, in the case that the image type of the medical image of the target object is type I, the image processing mode is the adjustment of definition and contrast of the medical image, and/or, image contouring. In the case that the image type of the medical image of the target object is type II, type III, or type IV, the image processing mode is the adjustment of definition and contrast adjustment of the medical image, and/or, image registration, and/or, image contouring.

In S205, a processing result is acquired by processing, without acquiring a user operation, the medical image using an image processing mode corresponding to the medical image of the target object.

in the embodiments of the present disclosure, the server end 01 acquires the processing result by processing, without acquiring any user operation, the medical image using the image processing mode corresponding to the medical image of the target object.

In some embodiments, the image processing mode includes image registration, image contouring, and adjustment of definition and contrast of the image. Correspondingly, the processing result includes a registration result of image registration, a contouring result of image contouring, and an image with adjusted definition and contrast.

In some embodiments, the server end 01 acquires a contouring result of the medical image of the target image by performing, without acquiring the user operation, image contouring (automatic image contouring) on the medical image of the target object.

In S206, the processing result is output in response to acquiring the user operation triggered by the user for viewing the processed medical image.

The user who wants to view the processing result may trigger, via the user end 02, a user operation for viewing the processed medical image. The server end 01 outputs the processing result in response to acquiring the user operation triggered by the user for viewing the processed medical image. Furthermore, the user end 02 acquires and displays the processing result. Thus, the user develops a radiation treatment plan based on the content displayed by the user end 02.

In some embodiments, the user operation is an operation for opening software in the user end 02 by the user.

in summary, the embodiments of the present disclosure provide the method for processing the medical image. in the method, the processing result is acquired by processing, without acquiring the user operation, the acquired medical image of the target object, and subsequently, the processing result is output in response to acquiring the user operation triggered by the user for viewing the processed medical image. That is, in method for processing the medical image according to the embodiments of the present disclosure, the medical image is automatically processed without acquiring the user operation, and thus a high efficiency of image processing is achieved.

Figure 6:
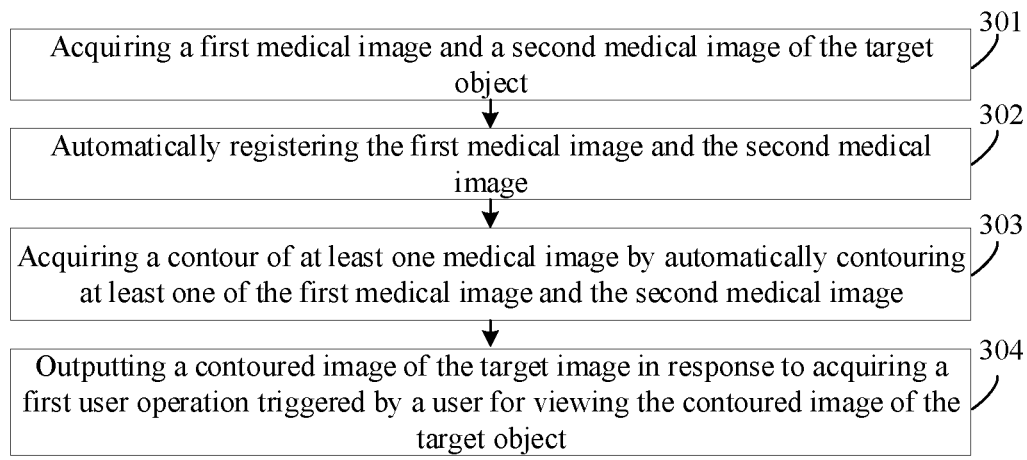
FIG. 6 is a flowchart of yet another method for processing a medical image according to some embodiments of the present disclosure.

FIG. 6 is a flowchart of a method for processing a medical image according to some embodiments of the present disclosure. The method is applicable to the server end 01 in the system for processing the medical image shown in FIG. 1. That is, the server 01 may implement the following method for processing the medical image. Referring to FIG. 6, the method includes the following steps.

In S301, a first medical image and a second medical image of a target object are acquired.

In the case that the medical image of the target object includes the first medical image and the second medical image, and the image types of both the first medical image and the second medical image are type II, type III or type IV, the server end 01 acquires the first medical image and the second medical image of the target object.

The first medical image and the second medical image are images acquired by imaging the target object using different imaging modes and/or in different time periods. That is, the first medical image and the second medical image are different from each other in at least one of the imaging mode and the imaging time.

In some embodiments, the imaging mode for imaging the target object includes CT, MR, and PET-CT, and the time period for imaging the target object includes before and after treatment, or different moments in adaptive radiation treatment. The target object is an affected part of a patient, or a model of the affected part.

In S302, the first medical image and the second medical image are automatically registered.

In the embodiments of the present disclosure, the server end 01 automatically registers the acquired first medical image and second medical image in response to acquiring the first medical image and the second medical image. The automatic registration indicates that the server end 01 registers the first medical image and the second medical image without acquiring any user operation.

In S303, a contour of at least one medical image is acquired by automatically contouring at least one of the first medical image and the second medical image.

In the embodiments of the present disclosure, the server end 01 acquires, in response to acquiring the first medical image and the second medical image, the contour of at least one medical image by automatically contouring at least one of the first medical image and the second medical image. The automatic contouring indicates that the server end 01 contours at least one of the first medical image and the second medical image without acquiring any user operation.

In some embodiments, the server end 01 acquires a first contour of the first medical image by automatically contouring the first medical image. In some embodiments, the server end 01 acquires a second contour of the second medical image by automatically contouring the second medical image. In some embodiments, the server end 01 acquires a first contour of the first medical image by automatically contouring the first medical image, and acquires a second contour of the second medical image by automatically contouring the second medical image.

In S304, a contoured image of the target image is output in response to acquiring a first user operation triggered by a user for viewing the contoured image of the target object.

In the embodiments of the present disclosure, the user who wants to view the contoured image of the target object triggers, via the user end 02, the first user operation for viewing the contoured image of the target object. The server end 01 outputs the contoured image of the target object in response to acquiring the first user operation triggered by the user for viewing the contoured image of the target object. Furthermore, the user end 02 acquires and displays the contoured image of the target object.

In some embodiments, the first user operation is an operation for opening software in the user end 02 by the user.

The contoured image of the target object is a superimposed image of the automatically registered first medical image and/or the automatically registered second medical image with the contour of the at least one medical image. In some embodiments, the contoured image of the target object is a superimposed image of the automatically registered first medical image with the contour of the at least one medical image. In some embodiments, the contoured image of the target object is a superimposed image of the automatically registered second medical image with the contour of the at least one medical image. In some embodiments, the contoured image of the target object is a superimposed image of the automatically registered first medical image and the automatically registered second medical image with the contour of at least one medical image.

Therefore, the user develops a radiation treatment plan based on the content displayed by the user end 02. For example, in the case that the user, after viewing the content displayed by the user end 02, believes that the contouring effect of the medical image is poor, the user manually modifies the contour to improve the accuracy of the contoured image, which further improves the accuracy of the developed radiation treatment plan.

In summary, the embodiments of the present disclosure provide the method for processing the medical image. In the method, the first medical image and the second medical image are acquired without acquiring any user operation, the first medical image and the second medical image are automatically registered, and the automatic contouring is performed on at least one of the first medical image and the second medical image. That is, in the method for processing the medical image according to the embodiments of the present disclosure, image acquisition, image registration and contouring are automatically performed without acquiring the user operation, and thus a high efficiency of image processing is achieved.

Figure 7:
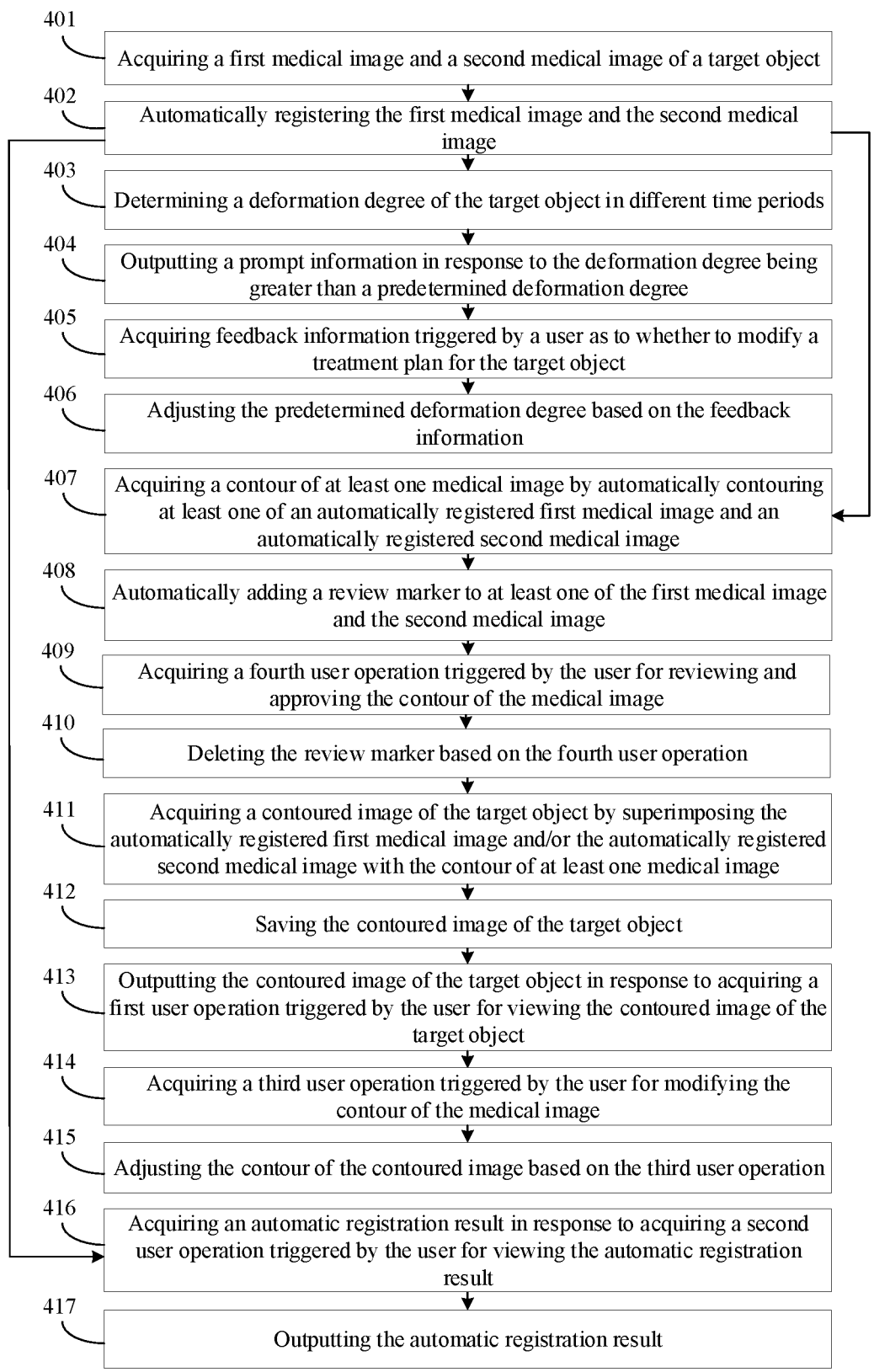
FIG. 7 is a flowchart of still another method for processing a medical image according to some embodiments of the present disclosure.

FIG. 7 is a flowchart of another method for processing a medical image according to some embodiments of the present disclosure. The method is applicable to the server end 01 in the system for processing the medical image shown in FIG. 1. That is, the server end 01 is capable of performing the method for processing the medical image described hereinafter. Referring to FIG. 7, the method includes S401 to S417.

In S401, a first medical image and a second medical image of a target object are acquired.

The server end 01 acquires the first medical image and the second medical image of the target object in a case that medical images of the target object include the first medical image and the second medical image, and the image types of the first medical image and the second medical image are type II, type III, or type IV.

The first medical image and the second medical image herein are images acquired by imaging the target object in different modes and/or in different time periods. That is, the first medical image differs from the second medical image in at least one of the imaging mode and the imaging time.

In some embodiments, the imaging mode for imaging the target object includes CT, MR, and PET-CT. The imaging time for imaging the target object includes: before and after the treatment, or different moments in the adaptive radiation treatment. The target object is an affected part of the patient or a model of the affected part.

It is assumed that the first medical image and the second medical image are images acquired by imaging the target object with different imaging modes at the same time. For example, the first medical image is an image acquired by imaging the target object with CT before the treatment, and the second medical image is an image acquired by imaging the target object with MR or PET-CT before the treatment.

It is assumed that the first medical image and the second medical image are images acquired by imaging the target object with the same imaging mode in different time periods. For example, in a case that the first medical image is an image acquired by imaging the target object with CT before the treatment, the second medical image is an image acquired by imaging the target object with CT after the treatment.

In some embodiments, the time or the places for the imaging are different when imaging the target object. For example, the first medical image and the second medical image are images acquired by imaging the target object with the same imaging mode in different time periods in different hospitals, respectively.

Figure 8:
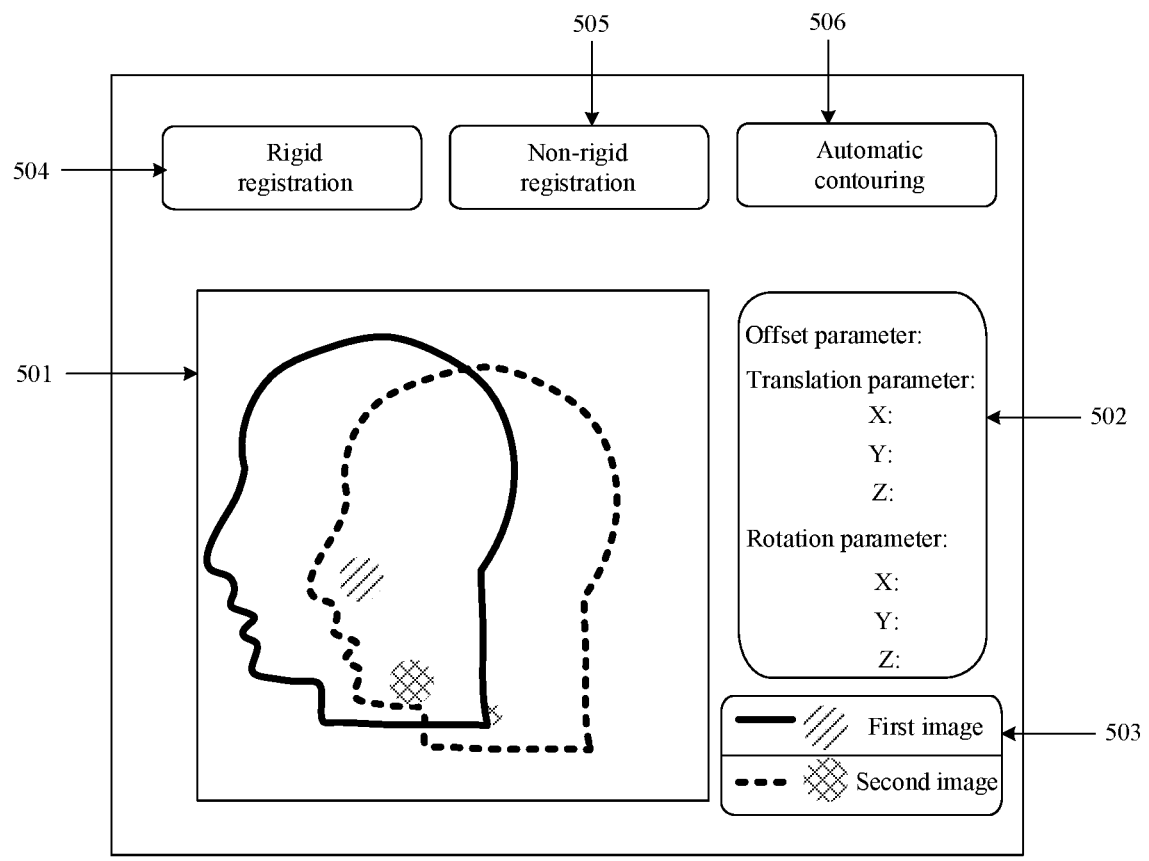
FIG. 8 is a schematic diagram of a display of a user end according to some embodiments of the present disclosure.

According to the embodiments of the present disclosure, after acquiring the first medical image and the second medical image, the server end 01 displays the first medical image and the second medical image on a display interface of a user end 02 in response to acquiring a user operation triggered by the user for viewing the first medical image and the second medical image. Referring to FIG. 8, the display interface includes an image display box 501, a parameter display box 502, and a prompt box 503. The image display box 501 displays the first medical image and the second medical image. The parameter display box 502 is configured to display an offset to be determined. The offset herein includes translation in the X, Y and Z directions, and rotation in the X, Y and Z directions. The prompt box 503 is configured to display prompt markers for the first medical image and the second medical image.

In S402, the first medical image and the second medical image are automatically registered.

According to the embodiments of the present disclosure, the server end 01 automatically registers, in response to acquiring the first medical image and the second medical image, the acquired first medical image and the second medical image. The automatic registration indicates that the server end 01 registers the first medical image and the second medical image without acquiring any user operation. In some embodiments, the automatic registration includes rigid registration and non-rigid registration.

The rigid registration herein refers to the registration without deforming the first medical image and the second medical image. For each of the first medical image and the second medical image, a distance between a first point and a second point not undergoing the rigid registration of the medical image is equal to a distance between the first point and the second point having undergone the rigid registration. The first point and the second point herein refer to any two points in the medical image.

In some embodiments, the server end 01 pre-stores a rigid registration model. The server end 01 rigidly registers, in response to acquiring the first medical image and the second medical image, the first medical image and the second medical image with the rigid registration model to acquire the offset between the first medical image and the second medical image.

In some embodiments, the offset includes a distance and an angle. The distance refers to a distance between a first target point in the first medical image and a second target point in the second medical image. The angle refers to an angle between a line between a third target point and a fourth target point in the first medical image, and a line between a fifth target point and a sixth target point in the second medical image. The first target point, the third target point, and the fourth target point are any point in the first medical image. The second target point is a point in the second medical image corresponding to the first target point, the fifth target point is a point in the second medical image corresponding to the third target point, and the sixth target point is a point in the second medical image corresponding to the fourth target point.

In some embodiments, the rigid registration model is acquired by training based on a plurality of rigidly registered sample image groups and a plurality of offsets. Each of the rigidly registered sample image groups herein includes two different medical images. The plurality of offsets are in one-to one correspondence to the plurality of rigidly registered sample image groups, and each offset refers to the offset between two medical images in the corresponding rigidly registered sample image group.

According to the embodiments of the present disclosure, the server end 01, after rigidly registering the first medical image and the second medical image, saves the offset acquired by the rigid registration.

Furthermore, the rigidly registered first medical image and the rigidly registered second medical image are further registered non-rigidly in response to rigidly registering the first medical image and the second medical image. The non-rigid registration (also be referred to as flexible registration or deformation registration) refers to the registration by deforming at least one of the first medical image and the second medical image. For each of the first medical image and the second medical image, the distance between the first point and the second point not undergoing the non-rigid registration in the medical image are not equal to the distance between the first point and the second point having undergone the non-rigid registration. The first point and the second point herein refer to any two points in the medical image.

In some embodiments, the server end 01 pre-stores a non-rigid registration model. In response to rigidly registering the first medical image and the second medical image, the rigidly registered first medical image and the rigidly registered second medical image are further registered non-rigidly with the non-rigid registration model to acquire a deformation field between the first medical image and the second medical image. The deformation field herein is configured to determine a relative deformation degree between the first medical image and the second medical image.

The non-rigid registration model is acquired by training based on a plurality of non-rigidly registered sample image groups and a plurality of deformation fields. Each of the non-rigidly registered sample image groups includes two different rigidly registered medical images. The plurality of deformation fields are in one-to one correspondence to the plurality of non-rigidly registered sample image groups, and each deformation field refers to a deformation field between two rigidly registered images in the corresponding non-rigidly registered sample image group.

According to the embodiments of the present disclosure, the server end 01, after non-rigidly registering the first medical image and the second medical image, saves the deformation field acquired by the non-rigid registration.

It should be noted that the offset acquired by the rigid registration and the deformation field acquired by the non-rigid registration are collectively referred to as the registration parameters. That is, the process that the server end 01 saves the offset acquired by the rigid registration and the deformation field acquired by the non-rigid registration indicates that the server end 01 saves the registration parameters acquired by automatically registering the first medical image and the second medical image.

After acquiring the offset by the rigid registration and the deformation field by the non-rigid registration, the first medical image and the second medical image are fused to complete the automatic registration of the first medical image and the second medical image. For example, the first medical image and the second medical image are fused by a pixel-level image fusion method based on the offset and deformation field. The fusion herein indicates that the first medical image and the second medical image are processed to extract the maximum amount of favorable information from the respective images, and thereby finally combined to form a high quality image.

In some embodiments, the pixel-level image fusion method includes an image fusion method based on non-multiscale transformations, an image fusion method based on multiscale transformations, and the like. The image fusion method based on non-multiscale transformations includes an averaging and weighted averaging method, an image fusion method by selecting larger (or smaller) pixel grayscale values, an image fusion method based on principal components analysis (PCA), an image fusion method based on modulation, and the like. The image fusion method based on multiscale transformations includes an image fusion method based on pyramid transformations, an image fusion method based on wavelet transformations, and the like.

In S403, a deformation degree of the target object in different time periods are determined.

According to the embodiments of the present disclosure, the first medical image and the second medical image are images acquired by imaging the target object in different time periods (the target object such as the tumor soft tissue changes in different time periods). That is, the image types of the first medical image and the second medical image are type II or type IV. In some embodiments, the first medical image and the second medical image are images acquired by imaging the target object with the same imaging mode or with different imaging modes. As the first medical image and the second medical image are images acquired by imaging the target object in different time periods, the server end 01 determines the deformation degree of the target object based on the first medical image and the second medical image.

In some embodiments, the server end 01 determines the deformation degree of the target object in different time periods based on the deformation fields acquired by rigidly registering the first medical image and the second medical image automatically. In some embodiments, the server end 01 determines the deformation degree of the target object in different time periods based on the overlap of the second medical image and the first contour of the first medical image in the superimposed image. In some embodiments, the server end 01 determines the deformation degree of the target object in different time periods based on the overlap of the first medical image and a second contour of the second medical image in the superimposed image.

In the case that the server end 01 is capable of determining the deformation degree of the target object in different time periods based on the overlap of the second medical image and the first contour of the first medical image in the superimposed image, it is defaulted that the server end 01 is capable of automatically contouring the first medical image. In the case that the server end 01 is capable of determining the deformation degree of the target object in different time periods based on the overlap of the first medical image and the second contour of the second medical image in the superimposed image, it is defaulted that the server end 01 is capable of automatically contouring the second medical image.

According to the embodiments of the present disclosure, the deformation degree is negatively correlated with the overlap of the first contour of the first medical image and the second medical image in the case that the server 10 is capable of determining the deformation degree of the target object in different time periods based on the overlap of the second medical image and the first contour of the first medical image in the superimposed image. That is, the greater the overlap of the first contour of the first medical image and the second medical image in the superimposed image, the smaller the deformation degree of the target object in different time periods; and the smaller the overlap of the first contour of the first medical image and the second medical image in the superimposed image, the greater the deformation degree of the target object in different time periods.

The deformation degree is negatively correlated with the overlap of the second contour of the second medical image and the first medical image in the case that the server 10 is capable of determining the deformation degree of the target object in different time periods based on the overlap of the first medical image and the second contour of the second medical image in the superimposed image. That is, the greater the overlap of the second contour of the second medical image and the first medical image in the superimposed image, the smaller the deformation degree of the target object in different time periods; and the smaller the overlap of the second contour of the second medical image and the first medical image in the superimposed image, the greater the deformation degree of the target object in different time periods.

In S404, a prompt information is output in response to the deformation degree being greater than the predetermined deformation degree.

According to the embodiments of the present disclosure, the predetermined deformation degree is a deformation degree pre-stored in the server end 01. In some embodiments, the predetermined deformation degree is a deformation degree determined by the user based on experience and stored in the server end 01.

In a case where the server end 01 determines that the deformation degree is greater than the predetermined deformation degree after comparing the deformation degree determined in S403 with the stored predetermined deformation degree, the server end 01 outputs the prompt information. As a result, the user end 02 acquires and displays the prompt information, and the user views the prompt information via the user end 02. The prompt information is configured to indicate whether the user modify the treatment plan of the target object.

In S405, feedback information triggered by the user as to whether to modify the treatment plan for the target object is acquired.

According to the embodiments of the present disclosure, the user selects to modify the treatment plan or not to modify the treatment plan after viewing the prompt information via the user end 02. In a case that the user wants to modify the treatment plan, the user triggers the feedback information of modifying the treatment plan for the target object. In a case that the user does not want to modify the treatment plan, the user triggers the feedback information of not modifying the treatment plan for the target object.

Furthermore, after the user triggers the feedback information as to whether to modify the treatment plan for the target object, the server end 01 acquires the feedback information triggered by the user as to whether to modify the treatment plan for the target object.

In S406, the predetermined deformation degree is adjusted based on the feedback information.

According to the embodiments of the present disclosure, the server end 01 adjusts, in response to acquiring the feedback information, the predetermined deformation degree based on the feedback information. For example, in a case that the server end 01 acquires the feedback information triggered by the user of modifying the treatment plan for the target object, the server end 01 determines that the size of the stored predetermined deformation degree is reasonable, such that no adjustment is required for the predetermined deformation degree. In a case that the server end 01 acquires the feedback information triggered by the user to not modify the treatment plan for the target object, the server end 01 determines that the size of the stored predetermined deformation degree is unreasonable, such that the predetermined deformation degree is adjusted (for example, the predetermined deformation degree is reduced).

In some embodiments, the server end 01 adjusts the predetermined deformation degree in response to acquiring once the feedback information triggered by a user of not modifying the treatment plan for the target object. In some embodiments, the server end 01 counts a number of times of continuously acquiring the feedback information triggered by the user of not modifying the treatment plan for the target object. In the case that the number of times of continuously acquiring the feedback information triggered by the user of not modifying the treatment plan for the target object is greater than a number threshold, the server end 01 adjusts the predetermined deformation degree. The number threshold is pre-stored in the server end 01 of the mobile terminal, or is set by the user.

The reliability of the adjustment is improved by counting the number of times of continuously acquiring the feedback information triggered by the user of not modifying the treatment plan for the target object, and then determining whether to adjust the predetermined deformation degree by comparing the number threshold with the number of times of continuously acquiring the feedback information triggered by the user of not modifying the treatment plan for the target object.

In S407, the contour of the at least one medical image is acquired by automatically contouring at least one of the automatically registered first medical image and the automatically registered second medical image.

According to the embodiments of the present disclosure, the server end 01 automatically contours, in response to automatically registering the first medical image and the second medical image, at least one of the automatically registered first medical image and the automatically registered second medical image to acquire the contour information of the at least one medical image. The automatic contouring indicates that the server end 01 contours at least one of the first medical image and the second medical image without acquiring any user operation.

In some embodiments, the server end 01 automatically contours the first medical image to acquire a first contour of the first medical image. In some embodiments, the server end 01 automatically contours the second medical image to acquire a second contour of the second medical image. In some embodiments, the server end 01 automatically contours the first medical image to acquire the first contour of the first medical image and automatically contours the second medical image to acquire the second contour of the second medical image.

In some embodiments, the server end 01 pre-stores a first contour model that may automatically contour the image acquired by the first imaging mode. Assuming that both the first medical image and the second medical image are images acquired by imaging the target object with the first imaging mode, the server end 01 automatically contours, in response to acquiring the first medical image, the first medical image and the second medical image with the first contour model to acquire first contour data of the first medical image and second contour data of the second medical image.

In some embodiments, the first medical image includes three-dimensional data, and the first contour of the first medical image is acquired based on the three-dimensional data of the first medical image. In addition, the first contour data of the first medical image also includes three-dimensional data different from the three-dimensional data in the first medical image. Accordingly, the second medical image includes three-dimensional data, and the second contour data of the second medical image is acquired based on the three-dimensional data of the second medical image. In addition, the second contour data of the second medical image also includes three-dimensional data different from the three-dimensional data in the second medical image.

In some embodiments, the first contour model is acquired by training based on the contour data of a plurality of contoured first sample images. In addition, the first medical image, the second medical image, and the first sample image are acquired by imaging with the first imaging mode.

In some embodiments, the contour data of the first sample image is acquired by identifying, by the server end 01, a contour manually contoured by the physician. The first sample image includes three-dimensional data, and the contour data of the first sample image is acquired based on the three-dimensional data of the first sample image. In addition, the contour data of the first sample image also includes three-dimensional data different from the three-dimensional data in the first sample image.

In some embodiments, the server end 01 generates a first contour file (RTstrust) based on the first contour data of the first medical image. The first contour file includes the first contour data of the first medical image, and the first contour data of the first medical image includes a plurality of first data points. In addition, the first contour file further includes an identifier (such as, a device number) of the device from which the first medical image is imaged, and information such as the name and age of the patient to whom the first medical image belongs. Accordingly, the server end 01 generates a second contour file based on the second contour data of the second medical image. The second contour file includes the second contour data of the second medical image, and the second contour data of the second medical image includes a plurality of second data points. In addition, the second contour file further includes an identifier (such as, a device number) of the device from which the second medical image is imaged, and information such as the name and age of the patient to whom the second medical image belongs.

Finally, the server end 01 sequentially connects, based on the first contour data of the first medical image, the plurality of first data points in the first contour data of the first medical image to acquire the first contour of the first medical image. As the first data points in the first contour data of the first medical image are scattered, the server end 01 interpolates the plurality of the first data points in the first contour data of the first medical image with an interpolation algorithm to acquire a plurality of first interpolated data points. Afterwards, the server end 01 sequentially connects the plurality of first data points of the first medical image and the plurality of first interpolated data points to acquire the first contour of the first medical image. Accordingly, the server end 01 sequentially connects, based on the second contour data of the second medical image, the plurality of second data points in the second contour data of the second medical image to acquire the second contour of the second medical image. As the second data points in the second contour data of the second medical image are scattered, the server end 01 interpolates the plurality of second data points in the second contour data of the second medical image with an interpolation algorithm to acquire a plurality of second interpolated data points. Afterwards, the server end 01 sequentially connects the plurality of second data points of the second medical image and the plurality of second interpolated data points to acquire the second contour of the second medical image.

In some embodiments, the server end 01 pre-stores a first contour model automatically contouring the image acquired by the first imaging mode. Assuming that the first medical image is an image acquired by imaging the target object with the first imaging mode, and the second medical image is an image acquired by imaging the target object with the second imaging mode, the server end 01 automatically contours, in response to acquiring the first medical image, the first medical image with the first contour model to acquire the first contour data of the first medical image. In addition, the server end 01 does not automatically contour the second medical image.

In this case, for the details of automatically contouring the first medical image by the server end 01, please refer to the related description of automatically contouring the first medical image by the server end 01 in above embodiments, which are not limited in the embodiments of the present disclosure.

In some embodiments, the server end 01 pre-stores a first contour model and a second contour model. The first contour model automatically contours the image acquired by the first imaging mode, and the second contour model automatically contours the image acquired by the second imaging mode. Assuming that the first medical image is an image acquired by imaging the target object with the first imaging mode, and the second medical image is an image acquired by imaging the target object with the second imaging mode, the server end 01 automatically contours, in response to acquiring the first medical image, the first medical image with the first contour model to acquire the first contour data of the first medical image and automatically contours the second medical image with the second contour model to acquire the second contour data of the second medical image.

In this case, for the details of automatically contouring the first medical image by the server end 01, please refer to the related description of automatically contouring the first medical image by the server end 01 in above embodiments, which are not limited in the embodiments of the present disclosure.

Furthermore, in some embodiments, the second contour model is acquired by training based on the contour data of a plurality of contoured second sample images. In addition, the second medical image and the second sample image are both acquired by imaging with the second imaging mode.

In some embodiments, the contour data of the second sample image is acquired by identifying, by the server end 01, a contour manually contoured by the physician. The second sample image includes three-dimensional data, and the contour data of the second sample image is acquired based on the three-dimensional data of the second sample image. In addition, the contour data of the second sample image also includes three-dimensional data different from the three-dimensional data in the second sample image.

Afterwards, the server end 01 generates a second contour file based on the second contour data of the second medical image. The second contour file includes the second contour data of the second medical image, and the second contour data of the second medical image includes a plurality of second data points. In addition, the second contour file further includes an identifier (such as, a device number) of the device from which the second medical image is imaged, and information such as the name and age of the patient to whom the second medical image belongs.

Finally, the server end 01 sequentially connects, based on the second contour data of the second medical image, the plurality of second data points in the second contour data of the second medical image to acquire the second contour of the second medical image. As the second data points in the second contour data of the second medical image are scattered, the server end 01 interpolates the plurality of second data points in the second contour data of the second medical image with an interpolation algorithm to acquire a plurality of second interpolated data points. Afterwards, the server end 01 sequentially connects the plurality of second data points of the second medical image and the plurality of second interpolated data points to acquire the second contour of the second medical image.

In some embodiments, the second contour model and the first contour model are different models, and contour the images acquired by imaging with different imaging modes. For example, the first contour model contours the image acquired by imaging the target object with CT, and the second contour model contours the image acquired by imaging the target image with MR.

According to the embodiments of the present disclosure, the first medical image is a planned image in the treatment plan for the target object, and the second medical image is a real-time image acquired by the imaging apparatus of the radiation treatment device. That is, the first medical image is an image acquired before the second medical image, and the user has already developed a corresponding treatment plan based on the first medical image. In this case, the server end 01 automatically contours the first medical image (such as, according to the above embodiments), such that the user develops a radiation treatment plan based on the first contouring result of the first medical image.

According to the embodiments of the present disclosure, in the case that the server end 01 determines that the deformation degree is greater than the predetermined deformation degree based on S404, it is indicated that the currently imaged second medical image changes a lot relative to the previously imaged first medical image. Thus, a poor treatment effect is caused in the case that the treatment is performed according to the treatment plan determined by the first contour of the first medical image. In the case that the server end 01 determines that the deformation degree is greater than the predetermined deformation degree, and acquires the feedback information triggered by the user of modifying the treatment plan for the target object, it is further indicated that the currently imaged second medical image changes a lot relative to the previously imaged first medical image. Thus, a poor treatment effect is caused in the case that the treatment is performed according to the treatment plan determined by the first contour of the first medical image.

In some embodiments, S407 includes automatically contouring the first medical image to acquire the first contour of the first medical image. In addition, the server end 01 automatically contours, in response to the deformation degree is greater than the predetermined deformation degree, the second medical image to acquire the second contour of the second medical image. By automatically contouring the second medical image, the user develops a new treatment plan based on the second contour of the second medical image, which ensures the reliability of the new treatment plan and the treatment effect.

In some embodiments, S407 includes automatically contouring the first medical image to acquire the first contour of the first medical image. In addition, in the case that the server end 01 determines that the deformation degree is greater than the predetermined deformation degree, and acquires the feedback information triggered by the user of modifying the treatment plan for the target object, the second medical image is automatically contoured to acquire the second contour of the second medical image. In the solutions, the second medical image is automatically contoured only in response to the deformation degree being greater than the predetermined deformation degree and acquiring the feedback information triggered by the user of modifying the treatment plan for the target object. As a result, the resources on the server end 01 are reduced, and the user is allowed to develop a new treatment plan based on the second contour of the second medical image, which ensures the reliability of the new treatment plan and the treatment effect.

In some embodiments, S407 includes automatically contouring the first medical image to acquire the first contour of the first medical image. In the case that the server end 01 determines that the deformation degree is greater than the predetermined deformation degree, the server end 01 adjusts the contour of the first medical image based on the deformation field acquired by automatically and non-rigidly registering the first medical image and the second medical image, such that the second contour of the second medical image is acquired.

In some embodiments, S407 includes automatically contouring the first medical image to acquire the first contour of the first medical image. In addition, in the case that the server end 01 determines that the deformation degree is greater than the predetermined deformation degree, and acquires the feedback information triggered by the user of modifying the treatment plan for the target object, the server end 01 adjusts the contour of the first medical image based on the deformation field acquired by automatically and non-rigidly registering the first medical image and the second medical image, such that the second contour of the second medical image is acquired. The second contour of the second medical image is acquired by adjusting the first contour of the first medical image, such that the time of acquiring the second contour is saved, and the efficiency is improved.

In S408, a review marker is automatically added to at least one of the first medical image and the second medical image.

According to the embodiments of the present disclosure, the server end 01 automatically adds a review marker to at least one automatically contoured medical image in automatically contouring the at least one of the first medical image and the second medical image, or after automatically contouring the at least one of the first medical image and the second medical image. The review marker is configured to indicate that the contour of the at least one medical image has not been reviewed and approved by the user.

In some embodiments, assuming that the server end 01 automatically contours the first medical image, the review marker is automatically added to the first medical image.

In S409, a fourth user operation triggered by the user for reviewing and approving the contour of the medical image is acquired.

According to the embodiments of the present disclosure, the user reviews the contour of the at least one medical image after the server end 01 automatically adds the review marker to at least one of the first medical image and the second medical image. In a case that the user triggers the fourth user operation for reviewing and approving the contour of the medical image, the server end 01 acquires the fourth user operation triggered by the user for reviewing and approving the contour of the medical image.

In S410, the review marker is deleted based on the fourth user operation.

According to the embodiments of the present disclosure, the server end 01 deletes the review marker based on the fourth user operation in response to acquiring the fourth user operation triggered by the user for reviewing and approving the contour of the medical image. Deleting the review marker indicates that the contour of the medical image has been reviewed and approved by the user.

In S411, a contoured image of the target object is acquired by superimposing the automatically registered first medical image and/or the automatically registered second medical image with the contour of at least one medical image.

According to the embodiments of the present disclosure, the server end 01 acquires the contoured image of the target object by superimposing the automatically registered first medical image with the contour of the at least one medical image. That is, the contoured image of the target object is a superimposed image of the automatically registered first medical image with the contour of the at least one medical image. In some embodiments, the server end 01 acquires the contoured image of the target object by superimposing the automatically registered second medical image with the contour of the at least one medical image. That is, the contoured image of the target object is a superimposed image of the contour of the automatically registered second medical image with the at least one medical image. In some embodiments, the server end 01 acquires the contoured image of the target object by superimposing the automatically registered first medical image and the automatically registered second medical image with the contour of the at least one medical image. That is, the contoured image of the target object is a superimposed image of the automatically registered first medical image and the automatically registered second medical image with the contour of the at least one medical image. The contour of the at least one medical image in the superimposed image in S411 is reviewed and approved by the user.

In a case that only the first contour of the first medical image is acquired in S407, the server end 01 superimposes the automatically registered first medical image and/or the automatically registered second medical image with the first contour of the first medical image. In a case that only the second contour of the second medical image is acquired in S407, the server end 01 superimposes the automatically registered first medical image and/or the automatically registered second medical image with the second contour of the second medical image. In a case that the first contour of the first medical image and the second contour of the second medical image are acquired in S407, the automatically registered first medical image and/or the automatically registered second medical image are superimposed with one of the contours of the medical images, so as to preventing the simultaneous display of two contours of the medical images from affecting each other.

In addition, as the second contour of the second medical image is acquired in the case that the server end 01 determines that the deformation degree is greater than the predetermined deformation degree, or in the case that the server end 01 determines that the deformation degree is greater than the predetermined deformation degree and acquires the feedback information triggered by the user of modifying the treatment plan for the target object, the accuracy of the first contour of the first medical image is poor. Thus, the automatically registered first medical image and/or the automatically registered second medical image are superimposed with the second contour of the second medical image.

According to the embodiments of the present disclosure, the server end 01 first performs automatic registration, and then performs automatic contouring, such that the automatically contoured contour is directly superimposed with the first medical image and/or the second medical image, the process is simple, and the effect is great.

Two cases may occur in the case that the server end 01 performs automatic contouring before the automatic registration, the first medical image is a reference image, and the second medical image is a floating image. In the first case, the server end 01 acquires the first contour of the first medical image by automatically contouring the first medical image, then automatically registers the first medical image and the second medical image, and directly superimposes the first contour of the first medical image with the automatically registered first medical image and/or the automatically registered second medical image. In the second case, the server end 01 acquires the second contour of the second medical image by automatically contouring the second medical image, then automatically registers the first medical image and the second medical image, and the second contour of the second medical image is superimposed with the automatically registered first medical image and/or the automatically registered second medical image only after being moved based on the registration parameters (offset and deformation field). As a result, in the case that the automatic contouring is performed before the automatic registration, the complexity of the process is increased, and the efficiency is low.

In S412, the contoured image of the target object is saved.

According to the embodiments of the present disclosure, after the contoured image of the target object is acquired in the S411, the contoured image of the target object is saved, such that the contoured image is quickly output in response to the requests of the user for viewing the contoured image at the user end 02, thereby resulting in a high efficiency and a great user experience.

In S413, the contoured image of the target object is output in response to acquiring the first user operation triggered by the user for viewing the contoured image of the target object.

According to the embodiments of the present disclosure, the user selects to view the contoured image of the target object via the user end 02 after the contoured image of the target object is saved on the server end 01. In this case, the user triggers the first user operation for viewing the contoured image of the target object via the user end 02, and the server end 01 outputs the contoured image of the target object in response to acquiring the first user operation. As a result, the user 02 acquires and displays the contoured image output by the server end 01. That is, the user views the contoured image via the user end 02.

Figure 9:
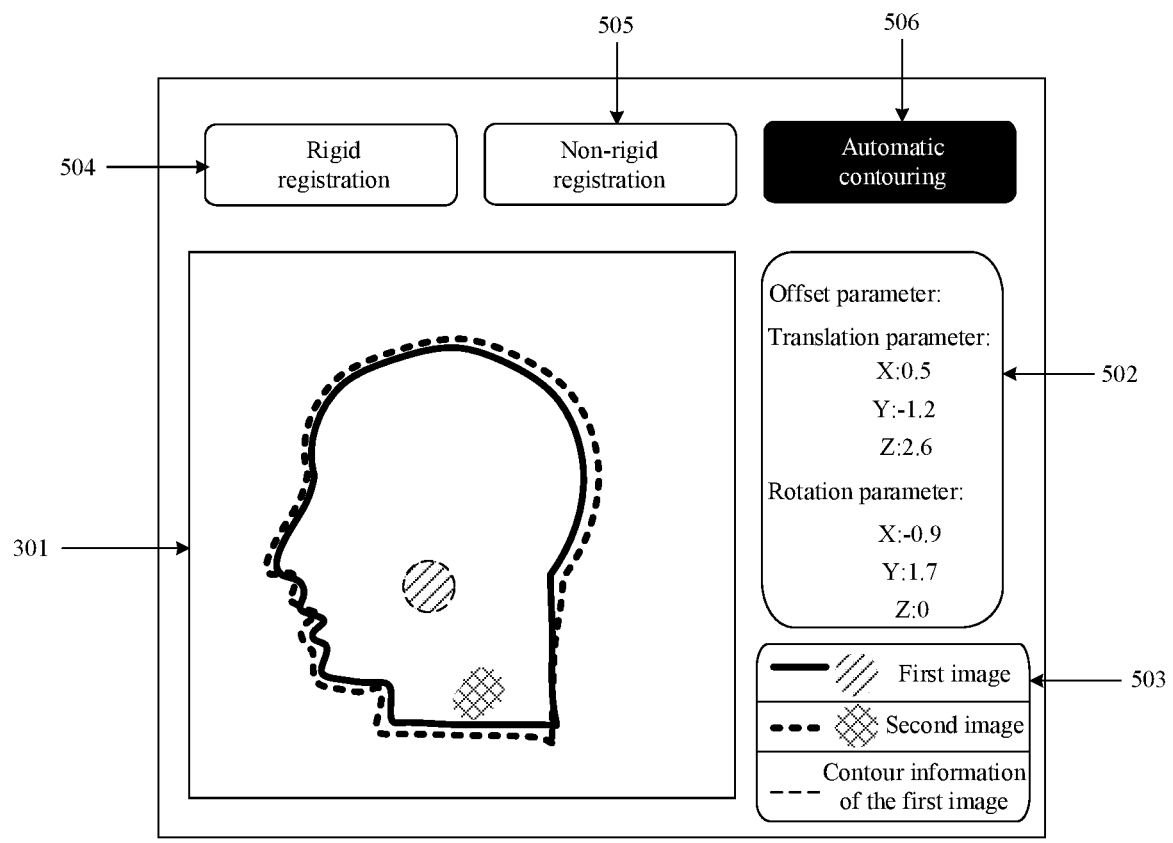
FIG. 9 is a schematic diagram of a display of another user end according to some embodiments of the present disclosure.

Referring to FIG. 9, the user end 02 displays an image display box 501, a parameter display box 502, and a prompt box 503. The image display box 501 displays the contoured image. Assuming that the contour in the contoured image is the first contour of the first medical image, the first contour of the first medical image shown in FIG. 9 includes the contour of an organ. The organ in FIG. 9 is represented by a circle. The parameter display box 502 displays values of the offset. In FIG. 9, for the offset, the translation amount X is 0.5, Y is −1.2, and Z is 2.6, and the rotation amount X is 0.9, Y is 1.7, and Z is 0.

It is assumed that the server end 01 is only able to automatically contour the first medical image to acquire the first contour of the first medical image. In some embodiments, the user end 02 displays the superimposed image of the first contour with the automatically registered first medical image, the superimposed image of the first contour with the automatically registered second medical image, and the superimposed image of the first contour with the automatically registered first medical image and the automatically registered second medical image. In some embodiments, the user end 02 displays three image display boxes. The first image display box is configured to display the superimposed image of the first contour with the automatically registered first medical image. The second image display box is configured to display the superimposed image of the first contour with the automatically registered second medical image. The third image display box is configured to display the superimposed image of the first contour with the automatically registered first medical image and the automatically registered second medical image.

It is assumed that the server end 01 is only able to automatically contour the second medical image to acquire the second contour of the second medical image. In some embodiments, the user end 02 displays the superimposed image of the second contour with the automatically registered first medical image, the superimposed image of the second contour with the automatically registered second medical image, and the superimposed image of the second contour with the automatically registered first medical image and the automatically registered second medical image. In some embodiments, the user end 02 displays three image display boxes. The first image display box is configured to display the superimposed image of the second contour with the automatically registered first medical image. The second image display box is configured to display the superimposed image of the second contour with the automatically registered second medical image. The third image display box is configured to display the superimposed image of the second contour with the automatically registered first medical image and the automatically registered second medical image.

It is assumed that the server end 01 automatically contours the first medical image to acquire the first contour of the first medical image, and also automatically contours the second medical image to acquire the second contour of the second medical image. In order to prevent the simultaneous display of two contours of the medical images from affecting each other, the user end 02 displays the superimposed image of the first contour with the first medical image and/or the second medical image, or the superimposed image of the second contour with the first medical image and/or the second medical image.

In some embodiments, the user end 02 further displays a first contour selection control corresponding to the first contour of the first medical image and a second contour selection control corresponding to the second contour of the second medical image. It is assumed that the user end 02 displays the first contour by default. The user triggers a selection operation for the second contour selection control in the case of desiring to view the second contour of the second medical image. As a result, the server end 01 receives and responds to the selection operation for the second contour selection control, such that the user end 02 displays the second contour of the second medical image and cancels the display of the first contour of the first medical image. Afterwards, the user triggers the selection operation for the first contour selection control in the user end 02 in the case of desiring to re-view the first contour of the first medical image. The server end 01 then receives and responds to the selection operation for the first contour selection control, such that the user end 20 redisplays the first contour of the first medical image and cancels the display of the second contour of the second medical image.

In this case, assuming that the user end 02 displays the first contour, the user end 02 displays the superimposed image of the first contour with the automatically registered first medical image, the superimposed image of the first contour with the automatically registered second medical image, and the superimposed image of the first contour with the automatically registered first medical image and the automatically registered second medical image. In some embodiments, the user end 02 displays three image display boxes. The first image display box is configured to display the superimposed image of the first contour with the automatically registered first medical image. The second image display box is configured to display the superimposed image of the first contour with the automatically registered second medical image. The third image display box is configured to display the superimposed image of the first contour with the automatically registered first medical image and the automatically registered second medical image.

In S414, a third user operation triggered by the user for modifying the contour of the medical image is acquired.

According to the embodiments of the present disclosure, in case the user deems that the contour of the medical image is poorly contoured after viewing the contoured image via the user end 02, the user modifies the contour manually. For example, the user triggers the third user operation for modifying the contour of the medical image via the user end 02.

In some embodiments, the contour modified by the user is the contour displayed in the user end 02. For example, the contour displayed by the user end 02 is the first contour of the first medical image in the case that the contoured image is the superimposed image of the first contour of the first medical image with the automatically registered first medical image and/or the automatically registered second medical image (that is, the contoured image includes the first contour of the first medical image). Accordingly, the user triggers the user operation for modifying the first contour of the first medical image.

In some embodiments, assuming that all the three image display boxes in the user end 02 display the first contour, the user manually modifies the first contour of an image display box in the case that the user deems that the accuracy of the first contour of the first medical image is poor after viewing the contents displayed by the three image display boxes in the user end 02. That is, the user triggers the third user operation for modifying the first contour of the first medical image in any of the image display boxes.

In some embodiments, assuming that all the three image display boxes in the user end 02 display the second contour, the user manually modifies the second contour of an image display box in the case that the user deems that the accuracy of the second contour of the second medical image is poor after viewing the contents displayed by the three image display boxes in the user end 02. That is, the user triggers the third user operation for modifying the second contour of the second medical image in any of the image display boxes.

In S415, the contour of the contoured image is adjusted based on the third user operation.

According to the embodiments of the present disclosure, the server end 01 acquires the third user operation after the user triggers the third user operation for modifying the contour of the medical image via the user end 02. In addition, the server end 01 adjusts the contour in the contoured image based on the third user operation to ensure the accuracy of the contoured image and thereby improve the accuracy of the developed radiation treatment plan.

In some embodiments, in the case that all the three image display boxes in the user end display the first contour of the first medical image, and the user manually modifies the first contour of the first medical image in the second image display box, the user end 02 displays the modified first contour of the first medical image not only in the second image display box, but also in the first image display box and the third image display box.

In some embodiments, in the case that all the three image display boxes in the user end display the second contour of the second medical image, and the user manually modifies the second contour of the second medical image in the third image display box, the user end 02 displays the modified second contour of the second medical image not only in the third image display box, but also in the first image display box and the second image display box.

In S416, an automatic registration result is acquired in response to acquiring the second user operation triggered by the user for viewing the automatic registration result.

According to the embodiments of the present disclosure, the user triggers the second user operation for viewing the automatic registration result via the user end 02 in the case of desiring to view the automatic registration result of the first medical image and the second medical image. Afterwards, the server end 01 acquires the automatic registration result in response to acquiring the second user operation. The automatic registration result is a superimposed image of the automatically registered first medical image with the automatically registered second medical image.

In some embodiments, the automatic registration result includes a registration result of the rigid registration and a registration result of the non-rigid registration. The registration result of the rigid registration refers to the superimposed image of the rigidly registered first medical image and the rigidly registered second medical image, and the registration result of the non-rigid registration refers to the superimposed image of the non-rigidly registered first medical image and the non-rigidly registered second medical image.

Accordingly, the second user operation triggered by the user for viewing the automatic registration result includes a first sub-operation for viewing the registration result of the rigid registration, and a second sub-operation for viewing the registration result of the non-rigid registration. The server end 01 acquires the registration result of the rigid registration in response to acquiring the first sub-operation. The server end 01 acquires the registration result of the non-rigid registration in response to acquiring the second sub-operation.

According to the embodiments of the present disclosure, there are two modes for acquiring the automatic registration result. In the first mode, the server end 01, after automatically registering the first medical image and the second medical image, superimposes and saves the automatically registered first medical image and the automatically registered second medical image. Thus, the pre-stored superimposed image of the first medical image and the second medical image is directly acquired in response to triggering the second user operation for viewing the automatic registration result by the user. In the second mode, the server end 01, after automatically registering the first medical image and the second medical image, merely saves the registration parameters for the automatic registration. Thus, when the user triggers the second user operation for viewing the automatic registration result, the server end 01 first acquires the pre-stored registration parameters and adjusts the position of the first medical image or the second medical image based on the registration parameters to generate the automatic registration result. For example, the server end 01 adjusts the position of the second medical image (assuming that the second medical image is a floating image and the first medical image is a reference image), and superimposes the first medical image with the second medical image to acquire a superimposed image of the first medical image and the second medical image (that is, generate an automatic registration result).

In S417, the automatic registration result is output.

According to the embodiments of the present disclosure, the server end 01 outputs the automatic registration result in response to acquiring the automatic registration result. As a result, the user end 02 acquires and displays the automatic registration result, such that the user determines the accuracy of the automatic registration result.

Figure 10:
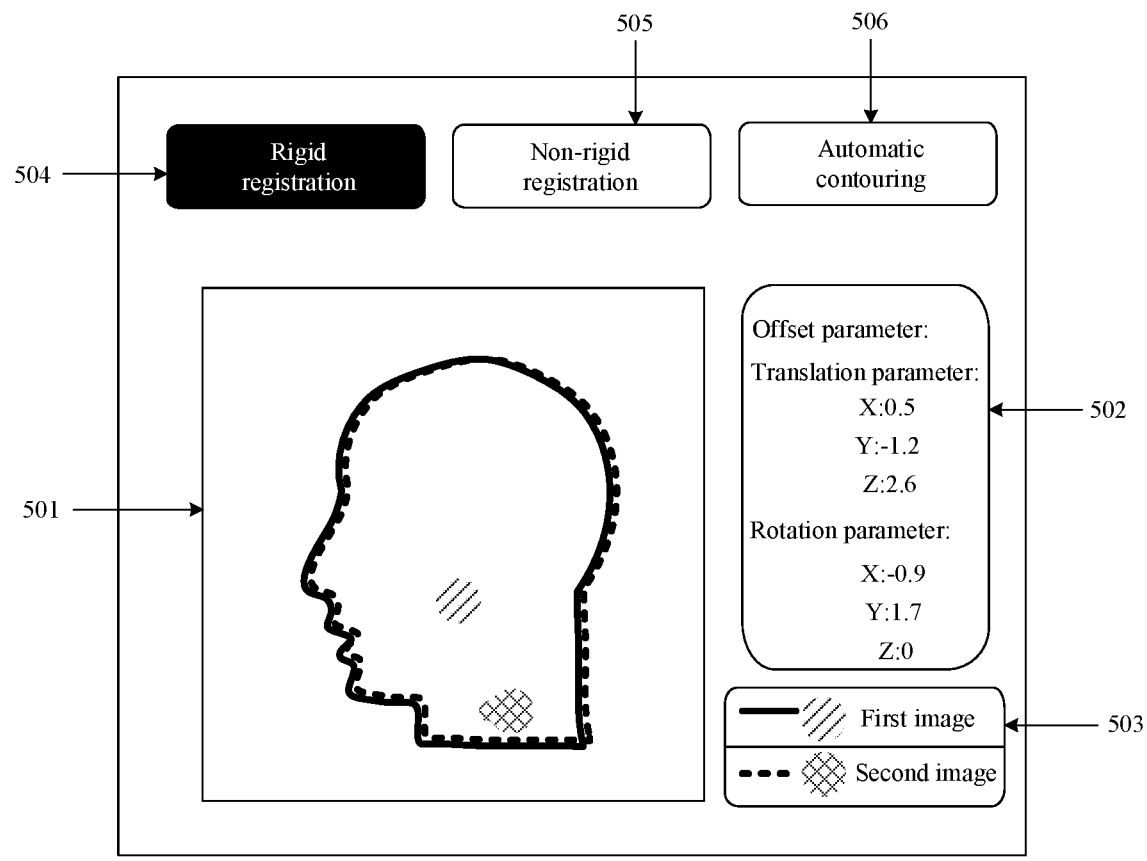
FIG. 10 is a schematic diagram of a display of yet another user end according to some embodiments of the present disclosure.

For example, referring to FIG. 10, the server end 01 acquires the first sub-operation for viewing the registration result of the rigid registration, and the user end 02 displays the registration result of the rigid registration. For example, the image display box 501 shows the superimposed image of the rigidly registered first medical image and the rigidly registered second medical image, and the parameter display box 502 shows the value of the offset. In FIG. 10, for the offset, the translation amount X is 0.5, Y is −1.2, and Z is 2.6, and the rotation amount X is 0.9, Y is 1.7, and Z is 0.

Figure 11:
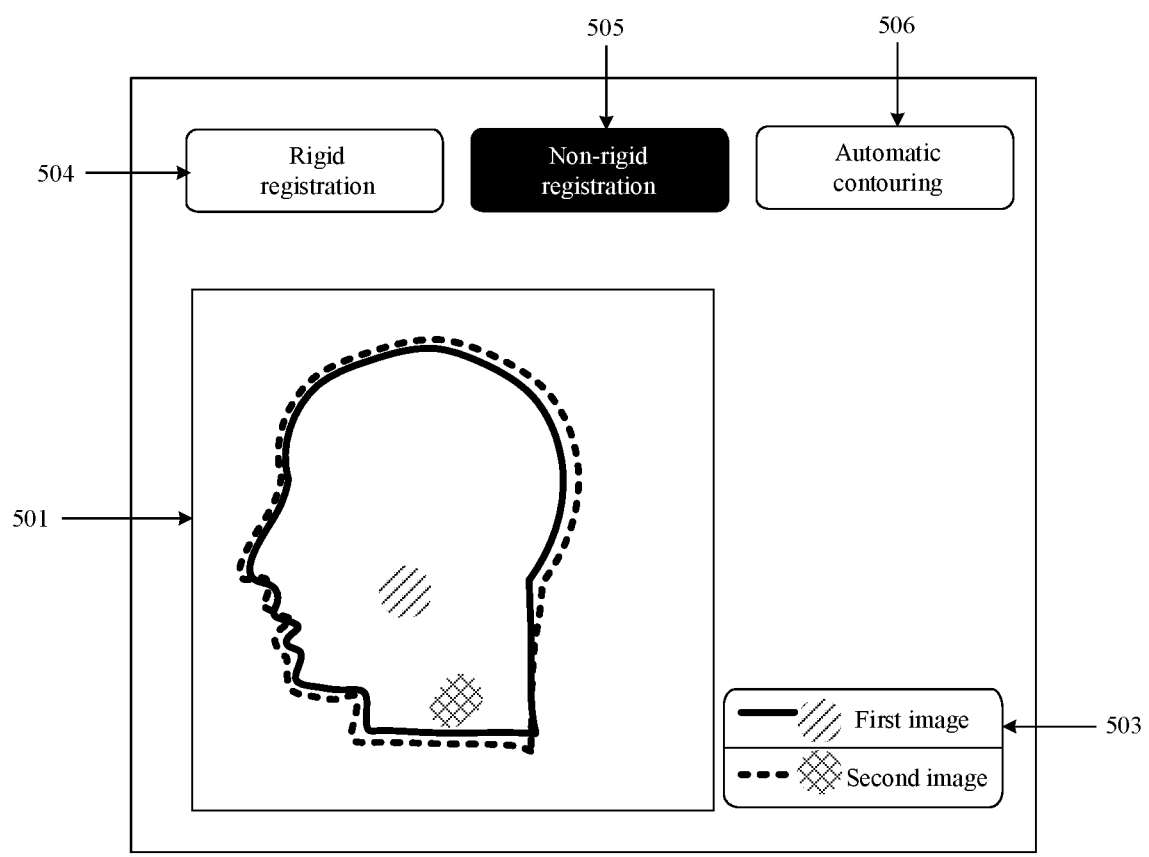
FIG. 11 is a schematic diagram of a display of still another user end according to some embodiments of the present disclosure.

Referring to FIG. 11, the server end 01 acquires the second sub-operation for viewing the registration result of the non-rigid registration, and the user end 02 displays the registration result of the non-rigid registration. For example, the image display box 501 displays the superimposed image of the non-rigidly registered first medical image and the non-rigidly registered second medical image. Referring to FIG. 11, the user end displays the image display box 501 and the prompt box 503, but does not display the parameter display box 502. FIG. 11, as compared to FIG. 10, shows that deformation occurs to either the first medical image or the second medical image in the image display box 501.

Referring to FIG. 10, the user end 01 acquires and displays the registration result of the rigid registration in response to acquiring, by the server end 01, the first sub-operation triggered by the user for viewing the registration result of the rigid registration. The user manually modifies the registration result of the rigid registration in the case that the user deems that the registration result of the rigid registration is poor after viewing the registration result of the rigid registration. For example, the user triggers the fourth user operation for modifying the registration result of the rigid registration via the user end 02. The server end 01 acquires the fourth user operation and adjusts the registration result of the rigid registration based on the fourth user operation to ensure the accuracy of the registration result of the rigid registration.

In some embodiments, the fourth user operation is a modifying operation for the offset, or an adjustment operation for at least one of the first medical image and the second medical image. The adjustment operation herein includes at least one of a translating operation and a rotating operation for at least one of the first medical image and the second medical image via the mouse or the keyboard. Upon adjusting one of the first medical image and the second medical image, the offset between the first medical image and the second medical image changes.

According to the embodiments of the present disclosure, the registration result of the non-rigid registration is updated simultaneously after the registration result of the rigid registration is adjusted. In some embodiments, the process of updating the registration result of the non-rigid registration includes that the server end 01 non-rigidly re-registers the first medical image and the second medical image based on the adjusted offset, and thereby acquires the updated deformation field. Then, the server end 01 superimposes the first medical image with the second medical image based on the updated offset and the updated deformation field.

That is, the user views the registration result of the intermediate automatic registration or the contouring result of the automatic contouring, and manually modifies the inaccurate result, such that the accuracy of the developed radiation treatment plan is improved.

It is to be noted that, with reference to FIGS. 8 to 11, the user end 02 further displays a rigid registration prompt control 504, a non-rigid registration prompt control 505, and an automatic contour prompt control 506. The rigid registration prompt control 504, when highlighted (for example, in the case that the background is black and the text is white in the rigid registration prompt control 504 in FIG. 10), prompts the user that the current user end is displaying the registration result of the rigid registration. The non-rigid registration prompt control 505, when highlighted (for example, in the case that the background is black and the text is white in the non-rigid registration prompt control 505 in FIG. 10), prompts the user that the current user end is displaying the registration result of the non-rigid registration. The automatic contour prompt control 506, when highlighted (for example, in the case that the background is black and the text is white in the automatic contour prompt control 506 in FIG. 9), prompts the user that the current user end is displaying the contoured image.

It should also be noted that the sequence of steps in the method for contouring the medical image in the embodiments of the present disclosure may be adjusted appropriately, and the steps may be added or deleted accordingly. In some embodiments, S403 to S406 and S414 to S414 are deleted as appropriate. In some embodiments, S408 and S407 are performed simultaneously. In some embodiments, S416 and S417 are performed following any one of the S403 to S418. Any method change made within the technical scope disclosed in the present disclosure by the person skilled in the art should be included within the scope of protection of the present disclosure, and thus is not described in detail herein.

In summary, the embodiments of the present disclosure provide a method for processing a medical image. In the method, the first medical image and the second medical image are acquired without acquiring any user operation, the first medical image and the second medical image are automatically registered, and the automatic contouring is performed on at least one of the first medical image and the second medical image. That is, in the method for processing the medical image according to the embodiments of the present disclosure, image acquisition, image registration and contouring are automatically performed without acquiring the user operation, and thus a high efficiency of image processing is achieved.

Figure 12:
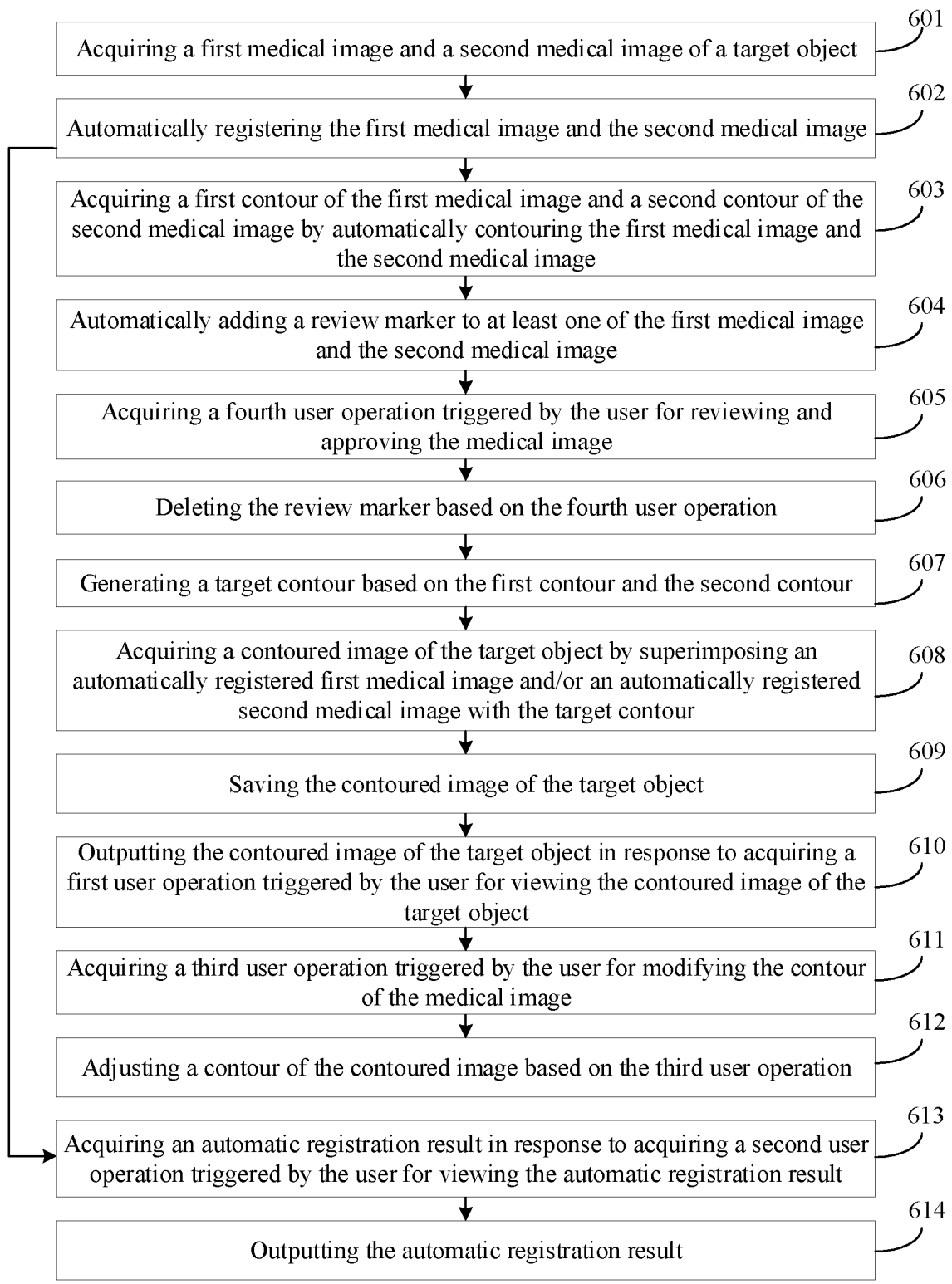
FIG. 12 is a flowchart of still yet another method for processing a medical image according to some embodiments of the present disclosure.

FIG. 12 is a flowchart of still yet another method for processing a medical image according to some embodiments of the present disclosure. The method is applicable to the server end 01 in the system for processing the medical image shown in FIG. 1. That is, the server end 01 is capable of performing the method for processing the medical image described below. Referring to FIG. 12, the method includes S601 to S614.

In S601, a first medical image and a second medical image of a target object are acquired.

According to the embodiments of the present disclosure, the specific process of S601 is referred to the specific description of S401, and thus is not repeated herein in the embodiments of the present disclosure.

In S602, the first medical image and the second medical image are automatically registered.

According to the embodiments of the present disclosure, the specific process of S602 is referred to the specific description of S402, and thus is not repeated herein in the embodiments of the present disclosure.

In S603, the first medical image and the second medical image are automatically contoured to acquire the first contour of the first medical image and the second contour of the second medical image.

According to the embodiments of the present disclosure, the first medical image and the second medical image are images acquired by imaging the target object with different imaging modes. For example, the first medical image is an image acquired by imaging the target object with CT, and the second medical image is an image acquired by imaging the target object with MR. Furthermore, the first medical image and the second medical image are images acquired by imaging the target object at the same time period, or images acquired by imaging the target object in different time periods.

In some embodiments, the server end 01 automatically contours, in response to automatically registering the first medical image and the second medical image, the automatically registered first medical image and the automatically registered second medical image to acquire the first contour of the first medical image and the second contour of the second medical image.

The specific process of automatically contouring the first medical image and the second medical image is referred to the specific description of the embodiments of S407, and thus is not repeated herein in the embodiments of the present disclosure.

In S604, a review marker is automatically added to at least one of the first medical image and the second medical image.

According to the embodiments of the present disclosure, the specific process of S604 is referred to the specific description of S408, and thus is not repeated herein in the embodiments of the present disclosure.

In S605, a fourth user operation triggered by the user for reviewing and approving the contour of the medical image is acquired.

According to the embodiments of the present disclosure, the specific process of S605 is referred to the specific description of S409, and thus is not repeated herein in the embodiments of the present disclosure.

In S606, the review marker is deleted based on the fourth user operation.

According to the embodiments of the present disclosure, the specific process of S606 is referred to the specific description of S410, and thus is not repeated herein in the embodiments of the present disclosure.

In S607, a target contour is generated based on the first contour and the second contour.

According to the embodiments of the present disclosure, the server end 01 generates, in response to acquiring the first contour of the first medical image and the second contour of the second medical image, a target contour based on the first contour and the second contour. Both the first contour and the second contour herein are reviewed and approved by the user.

In some embodiments, the target contour herein is one of the first contour and the second contour. In some embodiments, the target contour includes a partial contour of the first contour and a partial contour of the second contour, and the partial contour of the first contour is stitched with the partial contour of the second contour.

It is assumed that the first medical image is an image acquired by imaging the target object with CT, and the second medical image is an image acquired by imaging the target object with MR. In general, the bone tissue is quite visible in the image acquired by the CT imaging, such that the contour of the area of the bone tissue in the first medical image is rather clear. The soft tissue is quite visible in the image acquired by the MR imaging, such that the contour of the area of the soft tissue in the second medical image is rather clearer. Therefore, the target contour combines the advantages of the two images, and thereby be generated by stitching the contour of the area of the bone tissue in the first medical image with the contour of the area of the soft tissue in the second medical image.

In S608, a contoured image of the target object is acquired by superimposing the automatically registered first medical image and/or the automatically registered second medical image with the target contour.

According to the embodiments of the present disclosure, the server end 01 acquires the contoured image of the target object by superimposing the target contour with the automatically registered first medical image.

The server end 01 performs automatic registration, performs automatic contouring, and then acquires the target contour, such that the target contour is superimposed with the first medical image and/or the second medical image, the process is simple, and the effect is great.

In S609, the contoured image of the target object is saved.

According to the embodiments of the present disclosure, the specific process of S609 is referred to the specific description of S412, and thus is not repeated herein in the embodiments of the present disclosure.

In S610, the contoured image of the target object is output in response to acquiring the first user operation triggered by the user for viewing the contoured image of the target object.

According to the embodiments of the present disclosure, the specific process of the S610 is referred to the specific description of S413, and thus is not repeated herein in the embodiments of the present disclosure.

In S611, a third user operation triggered by the user for modifying the contour of the medical image is acquired.

According to the embodiments of the present disclosure, the user manually modifies the contour in the case that the user deems that the contour of the medical image is poorly contoured after viewing the contoured image via the user end 02. For example, the user triggers the third user operation for modifying the contour of the medical image via the user end 02.

In some embodiments, the contour modified by the user is the contour displayed in the user end 02. For example, the user triggers the user operation for modifying the target contour.

In S612, the contour of the contoured image is adjusted based on the third user operation.

According to the embodiments of the present disclosure, the specific process of S612 is referred to the specific description of S415, and thus is not repeated herein in the embodiments of the present disclosure.

In S613, an automatic registration result is acquired in response to acquiring the second user operation triggered by the user for viewing the automatic registration result.

According to the embodiments of the present disclosure, the specific process of S613 is referred to the specific description of S416, and thus is not repeated herein in the embodiments of the present disclosure.

In S614, the automatic registration result is output.

According to the embodiments of the present disclosure, the specific process of S614 is referred to the specific description of S417, and thus is not repeated herein in the embodiments of the present disclosure.

It should also be noted that the sequence of steps in the method for contouring the medical image in the embodiments of the present disclosure may be adjusted appropriately, and the steps may be added or deleted accordingly. In some embodiments, S603 to S607 are performed before S602, S604 and S603 are performed simultaneously; S613 and S614 are performed following any one of S603 to S612; and S610 to S614 are deleted as appropriate. Any method change made within the technical scope disclosed in the present disclosure by the person skilled in the art should be included within the scope of protection of the present disclosure, and thus is not described in detail herein.

In summary, the embodiments of the present disclosure provide a method for processing a medical image. In the method, the first medical image and the second medical image are acquired without acquiring any user operation, the first medical image and the second medical image are automatically registered, and the automatic contouring is performed on at least one of the first medical image and the second medical image. That is, in the method for processing the medical image according to the embodiments of the present disclosure, image acquisition, image registration and contouring are automatically performed without acquiring the user operation, and thus a high efficiency of image processing is achieved.

Figure 13:
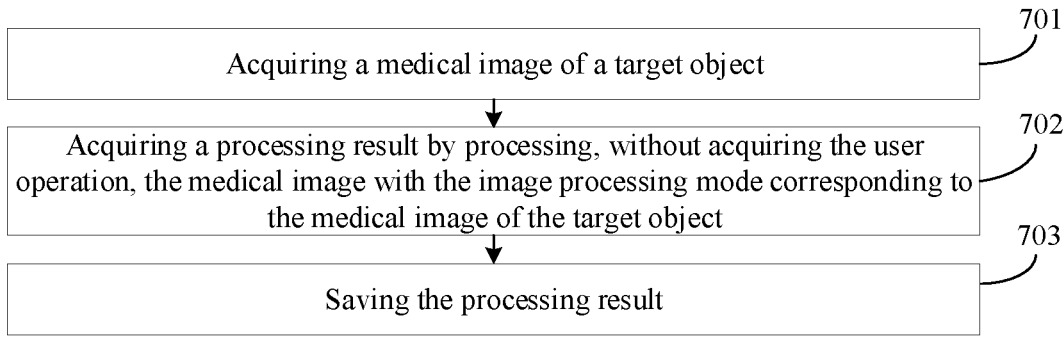
FIG. 13 is a flowchart of still yet another method for processing a medical image according to some embodiments of the present disclosure.

FIG. 13 is a flowchart of yet still another method for processing a medical image according to some embodiments of the present disclosure. The method is applicable to the server end 01 in the system for processing the medical image shown in FIG. 1. That is, the server end 01 is capable of performing the method for processing the medical image described below. Referring to FIG. 13, the method includes S701 to S703.

In S701, a medical image of a target object is acquired.

According to the embodiments of the present disclosure, the medical image of the target object is an image acquired by imaging the target object with an imaging apparatus. The server end 01 acquires the medical image of the target object from the imaging apparatus.

In some embodiments, the imaging apparatus is a separate apparatus or an imaging apparatus integrated in the radiation treatment device.

In S702, the processing result is acquired by processing, without acquiring the user operation, the medical image with the image processing mode corresponding to the medical image of the target object.

According to the embodiments of the present disclosure, the server end 01 acquires the processing result by processing, without acquiring the user operation, the medical image with the image processing mode corresponding to the medical image of the target object.

In some embodiments, the image processing mode includes: an adjustment of definition and contrast of the image, and/or image registration, and/or image contouring. Accordingly, the processing result includes: an image with adjusted sharpness and contrast, and/or a registration result of the image registration, and/or a contouring result of the image contouring. The processing result herein is an image or a parameter, such as, the offset and deformation field are acquired from the image registration.

In some embodiments, the server end 01 contours (that is, automatically contours) the medical image of the target object without acquiring the user operation to acquire the contouring result of the medical image of the target object.

In S703, the processing result is saved.

According to the embodiments of the present disclosure, the server end, after acquiring the processing result of the medical image of the target object, saves the processing result. As a result, the processing result is output quickly in response to triggering, by the user, the user operation for viewing the processed medical image, which facilitates the direct view of the user.

In summary, the embodiments of the present disclosure provide a method for processing a medical image. In the method, the processing result is acquired by processing the acquired medical image of the target object without acquiring the user operation. That is, in the method for processing the medical image according to the embodiments of the present disclosure, the medical image is automatically processed without acquiring the user operation, such that the efficiency is great, and the processing result is protected. Furthermore, in the method, the acquired processing result is saved upon the acquisition of the processing result, and thus the processing result is quickly output in response to triggering, by the user, the user operation for viewing the processed medical images, and the user experience is improved.

Figure 14:
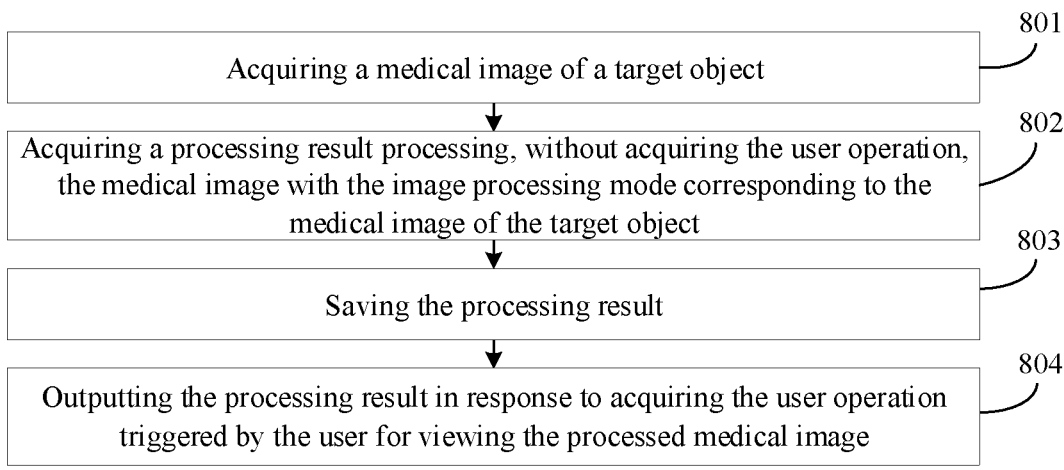
FIG. 14 is a flowchart of still yet another method for processing a medical image according to some embodiments of the present disclosure.

FIG. 14 is a flowchart of yet still another method for processing a medical image according to some embodiments of the present disclosure. The method is applicable to the server end 01 in the system for processing the medical image shown in FIG. 1. That is, the server end 01 is capable of performing the method for processing the medical image described below. Referring to FIG. 14, the method includes S801 to S804.

In S801, a medical image of a target object is acquired.

According to the embodiments of the present disclosure, the medical image of the target object is an image acquired by imaging the target object with an imaging apparatus. The server end 01 acquires the medical image of the target object from the imaging apparatus.

In some embodiments, the imaging apparatus is a separate apparatus or an imaging apparatus integrated in the radiation treatment device.

In S802, the processing result is acquired by processing, without acquiring the user operation, the medical image with the image processing mode corresponding to the medical image of the target object.

According to the embodiments of the present disclosure, the server end 01 acquires the processing result by processing, without acquiring the user operation, the medical image with the image processing mode corresponding to the medical image of the target object.

In some embodiments, the image processing mode includes image registration, and/or image contouring. Accordingly, the processing result includes a registration result of the image registration, and/or a contouring result of the image contouring.

In some embodiments, the server end 01 contours (that is, automatically contours) the medical image of the target object without acquiring the user operation to acquire the contouring result of the medical image of the target object.

In S803, the processing result is saved.

According to the embodiments of the present disclosure, the server end, after acquiring the processing result of the medical image of the target object, saves the processing result. As a result, the processing result is output quickly in response to triggering, by the user, the user operation for viewing the processed medical image, which facilitates the view of the user.

In S804, the processing result is output in response to acquiring the user operation triggered by the user for viewing the processed medical image.

According to the embodiments of the present disclosure, the user triggers the user operation for viewing the processed medical image at the user end 02 when desiring to view the processing result. The processing result is output in response to acquiring, by the server end 01, the user operation triggered by the user for viewing the processed medical image. Furthermore, the user end 02 acquires and displays the processing result. As a result, the user develops a radiation treatment plan based on the content displayed in the user end 02.

In some embodiments, the user operation is an operation of opening the software in the user end 02 by the user.

In summary, the embodiments of the present disclosure provide a method for processing a medical image. In the method, the processing result is acquired by processing the acquired medical image of the target object without acquiring the user operation. That is, in the method for processing the medical image according to the embodiments of the present disclosure, the medical image is automatically processed without acquiring the user operation, such that the efficiency is great, and the processing result is protected. Furthermore, in the method, the acquired processing result is saved upon the acquisition of the processing result, and thus the processing result is quickly output in response to triggering, by the user, the user operation for viewing the processed medical images, and the user experience is improved.

In the embodiments of the present disclosure, the detailed embodiments of the method for processing the medical image shown in FIG. 13 and FIG. 14 are referred to the method shown in FIGS. 5, 6, 7 and 12, and thus are not repeated herein in the embodiments of the present disclosure.

Figure 15:
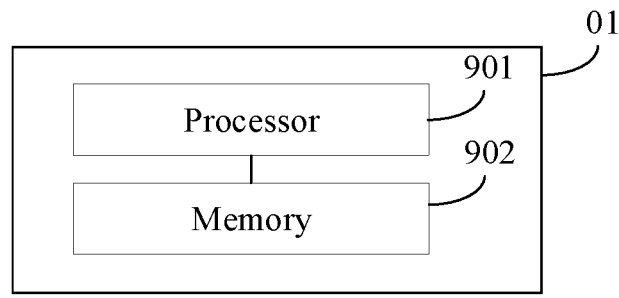
FIG. 15 is a schematic structural diagram of a server end according to some embodiments of the present disclosure.

FIG. 15 is a schematic structural diagram of a server end according to some embodiments of the present disclosure. Referring to FIG. 15, the server end 01 includes a processor 901, and a memory 902.

The memory 902 is configured to store an instruction to be executed by the processor 501. The processor 901, when executing the instruction stored in the memory 902, is caused to perform the method for processing the medical image according to the above embodiments, for example, the method shown in any one of FIGS. 4 to 7 and FIGS. 12 to 14.

The embodiments of the present application provide a non-volatile computer readable storage medium. The computer readable storage medium stores an instruction therein. The instruction, when executed on a computer, causes the computer to perform the method for processing the medical image according to the above embodiments, for example, the method shown in any one of FIGS. 4 to 7 and FIGS. 12 to 14.

The embodiments of the present disclosure provide a computer program product including an instruction. The instruction, when executed on a computer, causes the computer to perform the method for processing the medical image according to the above embodiments, for example, the method shown in any one of FIGS. 4 to 7 and FIGS. 12 to 14.

Described above are example embodiments of the present disclosure, and are not intended to limit the present disclosure. Any modifications, equivalent replacements, improvements and the like made within the spirit and principles of the present disclosure are included within the scope of protection of the present disclosure.

What is claimed is:

1. A method for processing a medical image, comprising:
acquiring a medical image of a target object;
determining an image type of the medical image of the target object; and
determining an image processing mode corresponding to the medical image of the target object based on the image type of the medical image of the target object and a predetermined corresponding relationship, wherein the predetermined corresponding relationship is a predefined corresponding relationship between the image type and the image processing mode;
acquiring a processing result by processing, without acquiring a user operation, the medical image using the image processing mode corresponding to the medical image of the target object; and
outputting the processing result in response to acquiring a user operation triggered by a user for viewing a processed medical image;
wherein the image type of the medical image of the target object comprises:
type I: an image acquired by imaging the target object using a same imaging mode in a same time period;
type II: an image acquired by imaging the target object using the same imaging mode in different time periods;
type III: an image acquired by imaging the target object using different imaging modes in the same time period; and
type IV: an image acquired by imaging the target object using different imaging modes in different time periods.

2. The method according to claim 1, wherein
the medical image of the target object comprises a first medical image and a second medical image;
in the case that the image types of both the first medical image and the second medical image are type II, type III or type IV, acquiring the processing result by processing the medical image using the image processing mode corresponding to the medical image of the target object comprises:
automatically registering the first medical image and the second medical image;
acquiring a contour of at least one medical image by automatically contouring at least one of the first medical image and the second medical image;
and outputting the processing result in response to acquiring the user operation triggered by the user for viewing the processed medical image comprises:
outputting, in response to acquiring a first user operation triggered by the user for viewing a contoured image of the target object, the contoured image of the target object, wherein the contoured image of the target object is a superimposed image of an automatically registered first medical image and/or an automatically registered second medical image with the contour of the at least one medical image.

3. The method according to claim 2, wherein acquiring the contour of the at least one medical image by automatically contouring at least one of the first medical image and the second medical image comprises:
acquiring the contour of the at least one medical image by automatically contouring at least one of the automatically registered first medical image and the automatically registered second medical image.

4. The method according to claim 2, wherein prior to acquiring the first user operation triggered by the user for viewing the contoured image of the target object, the method further comprises:
   acquiring the contoured image of the target object by superposing the automatically registered first medical image and/or the automatically registered second medical image with the contour of the at least one medical image; and
   saving the contoured image of the target object.

5. The method according to claim 2, wherein in the case that the image types of both the first medical image and the second medical image are type II or type IV, the method further comprises:
   determining a deformation degree of the target object in different time periods; and
   outputting a prompt information in response to the deformation degree being greater than a predetermined deformation degree, wherein the prompt information is configured to prompt the user whether to modify a treatment plan for the target object.

6. The method according to claim 5, wherein determining the deformation degree of the target object in different time periods comprises:
   determining the deformation degree of the target object in different time periods based on a deformation field acquired by automatic non-rigid registration of the first medical image and the second medical image;
   determining the deformation degree of the target object in different time periods based on an overlap of a first contour of the first medical image and the second medical image in the superimposed image; or
   determining the deformation degree of the target object in different time periods based on an overlap of a second contour of the second medical image and the first medical image in the superimposed image.

7. The method according to claim 5, further comprising:
   acquiring feedback information triggered by the user as to whether to modify the treatment plan for the target object; and
   adjusting the predetermined deformation degree based on the feedback information.

8. The method according to claim 5, wherein
   the first medical image is a planned image in the treatment plan for the target object, and the second medical image is a real-time image acquired by an imaging apparatus of a radiation treatment device;
   acquiring the contour of the at least one medical image by automatically contouring at least one of the first medical image and the second medical image comprises:
      acquiring a first contour of the first medical image by automatically contouring the first medical image;
   and in the case that the deformation degree is greater than the predetermined deformation degree, the method further comprises:
      acquiring a second contour of the second medical image by automatically contouring the second medical image.

9. The method according to claim 5, wherein
   the first medical image is a planned image in the treatment plan for the target object, and the second medical image is a real-time image acquired by an imaging apparatus of a radiation treatment device;
   acquiring the contour of the at least one medical image by automatically contouring at least one of the first medical image and the second medical image comprises:
      acquiring a first contour of the first medical image by automatically contouring the first medical image;
   and in the case that the deformation degree is greater than the predetermined deformation degree, and the feedback information triggered by the user for modifying the treatment plan for the target object is acquired, the method further comprises:
      acquiring a second contour of the second medical image by automatically contouring the second medical image.

10. The method according to claim 5, wherein
    the first medical image is a planned image in the treatment plan for the target object, and the second medical image is a real-time image acquired by an imaging apparatus of a radiation treatment device;
    acquiring the contour of the at least one medical image by automatically contouring at least one of the first medical image and the second medical image comprises:
       acquiring a first contour of the first medical image by automatically contouring the first medical image;
    and in the case that the deformation degree is greater than the predetermined deformation degree, the method further comprises:
       acquiring a second contour of the second medical image by adjusting the first contour based on a deformation field acquired by automatic non-rigid registration of the first medical image and the second medical image.

11. The method according to claim 5, wherein
    the first medical image is a planned image in the treatment plan for the target object, and the second medical image is a real-time image acquired by an imaging apparatus of a radiation treatment device;
    acquiring the contour of the at least one medical image by automatically contouring at least one of the first medical image and the second medical image comprises:
       acquiring a first contour of the first medical image by automatically contouring the first medical image;
    and in the case that the deformation degree is greater than the predetermined deformation degree, and the feedback information triggered by the user for modifying the treatment plan for the target object is acquired, the method further comprises:
       acquiring a second contour of the second medical image by adjusting the first contour based on a deformation field acquired by automatic non-rigid registration of the first medical image and the second medical image.

12. The method according to claim 2, wherein
    acquiring the contour of the at least one medical image by automatically contouring at least one medical image of the first medical image and the second medical image comprises:
       acquiring a first contour of the first medical image and a second contour of the second medical image by automatically contouring the first medical image and the second medical image;
    the method further comprises:
       generating a target contour based on the first contour and the second contour, wherein the contoured image of the target object is a superimposed image of the automatically registered first medical image and/or the automatically registered second medical image with the target contour.

13. The method according to claim 12, wherein the first medical image and the second medical image are images acquired by imaging the target object using different imaging modes.

14. The method according to claim 2, wherein outputting the processing result in response to acquiring the user operation triggered by the user for viewing the processed medical image further comprises:
acquiring an automatic registration result in response to acquiring a second user operation triggered by the user for viewing the automatic registration result, wherein the automatic registration result is a superimposed image of the automatically registered first medical image and the automatically registered second medical image; and
outputting the automatic registration result.

15. A device for processing a medical image, comprising: a processor and a memory configured to store an instruction executed by the processor, wherein the processor, when executing the instruction stored in the memory, is caused to perform the method for processing the medical image as defined in claim 1.

16. A non-transitory computer-readable storage medium, storing an instruction therein, wherein the instruction, when executed on a computer, causes the computer to perform the method for processing the medical image as defined in claim 1.

17. A method for processing a medical image, comprising:
acquiring a medical image of a target object;
determining an image type of the medical image of the target object; and
determining an image processing mode corresponding to the medical image of the target object based on the image type of the medical image of the target object and a predetermined corresponding relationship, wherein the predetermined corresponding relationship is a predefined corresponding relationship between the image type and the image processing mode;
acquiring a processing result by processing, without acquiring a user operation, the medical image using the image processing mode corresponding to the medical image of the target object, wherein the image processing mode comprises automatic registration and/or automatic contouring; and
saving the processing result;
wherein the image type of the medical image of the target object comprises:
type I: an image acquired by imaging the target object using a same imaging mode in a same time period;
type II: an image acquired by imaging the target object using the same imaging mode in different time periods;
type III: an image acquired by imaging the target object using different imaging modes in the same time period; and
type IV: an image acquired by imaging the target object using different imaging modes in different time periods.

18. A system for processing a medical image, comprising:
a server end and a user end;
wherein:
the server end is configured to acquire a medical image of a target object; determine an image type of the medical image of the target object; determine an image processing mode corresponding to the medical image of the target object based on the image type of the medical image of the target object and a predetermined corresponding relationship, wherein the predetermined corresponding relationship is a predefined corresponding relationship between the image type and the image processing mode; and acquire a processing result by processing, without acquiring a user operation, the medical image using the image processing mode corresponding to the medical image of the target object;
the user end is configured to acquire a user operation triggered by a user for viewing a processed medical image, and send the user operation to the server end;
the server end is further configured to output the processing result in response to acquiring the user operation; and
the user end is further configured to acquire the processing result and display a medical image corresponding to the processing result;
wherein the image type of the medical image of the target object comprises:
type I: an image acquired by imaging the target object using a same imaging mode in a same time period;
type II: an image acquired by imaging the target object using the same imaging mode in different time periods;
type III: an image acquired by imaging the target object using different imaging modes in the same time period; and
type IV: an image acquired by imaging the target object using different imaging modes in different time periods.

* * * * *